(12) United States Patent
Patek et al.

(10) Patent No.: US 12,144,658 B2
(45) Date of Patent: Nov. 19, 2024

(54) EVALUATION AND VISUALIZATION OF GLYCEMIC DYSFUNCTION

(71) Applicant: Dexcom, Inc., San Diego, CA (US)

(72) Inventors: Stephen D. Patek, Charlottesville, VA (US); Stephen J. Vanslyke, Carlsbad, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 18/219,845

(22) Filed: Jul. 10, 2023

(65) Prior Publication Data

US 2023/0346320 A1 Nov. 2, 2023

Related U.S. Application Data

(63) Continuation of application No. 16/721,810, filed on Dec. 19, 2019, now Pat. No. 11,696,728, which is a
(Continued)

(51) Int. Cl.
*A61B 5/00* (2006.01)
*G16H 10/60* (2018.01)
(Continued)

(52) U.S. Cl.
CPC .......... *A61B 5/7275* (2013.01); *A61B 5/4833* (2013.01); *G16H 10/60* (2018.01); *G16H 20/60* (2018.01); *G16H 50/30* (2018.01); *G16H 70/20* (2018.01); *A61B 5/14532* (2013.01); *A61M 2230/201* (2013.01); *C07K 14/62* (2013.01)

(58) Field of Classification Search
CPC . A61B 5/7275; A61B 5/4833; A61B 5/14532; A61B 5/4866; G16H 10/60; G16H 20/60; G16H 50/30; G16H 70/20; G16H 20/10; A61M 2230/201; C07K 14/62
See application file for complete search history.

(56) References Cited

U.S. PATENT DOCUMENTS 9,439,602 B2 9/2016 Sparacino et al.
2003/0028089 A1 2/2003 Galley et al.
(Continued)

FOREIGN PATENT DOCUMENTS

EP 2062527 A1 * 5/2009 ......... A61B 5/14532
JP 2014534483 A 12/2014
(Continued)

OTHER PUBLICATIONS

Zisser H. et al., "Bolus Calculator: A Review of Four 'Smart' Insulin Pumps", Diabetes Technology & Therapeutics, Dec. 2008; 10(6): 441-4 (Year: 2008).*
(Continued)

*Primary Examiner* — Linh Giang Le
(74) *Attorney, Agent, or Firm* — Stuart H. Mayer; Kaplan Breyer Schwarz LLP

(57) ABSTRACT

An amount of glycemic dysfunction associated with mis-timing (e.g., delay) of meal boluses based on replay analysis is determined. The amount of dysfunction of historical or estimated bolusing as compared to an optimally timed bolus based on the replay analysis is quantified and visualized. Inferences may be made about diabetes meal management regarding inputs from a patient.

48 Claims, 22 Drawing Sheets

Related U.S. Application Data continuation of application No. 16/721,679, filed on Dec. 19, 2019, now abandoned.

(60) Provisional application No. 62/786,149, filed on Dec. 28, 2018.

(51) Int. Cl.
  G16H 20/60 (2018.01)
  G16H 50/30 (2018.01)
  G16H 70/20 (2018.01)
  *A61B 5/145* (2006.01)
  *C07K 14/62* (2006.01)

(56) References Cited

U.S. PATENT DOCUMENTS

| | | | |
|---|---|---|---|
| 2010/0125241 A1* | 5/2010 | Prud'homme | G16H 20/17 600/300 |
| 2010/0295686 A1 | 11/2010 | Sloan et al. | |
| 2011/0021898 A1 | 1/2011 | Wei et al. | |
| 2011/0184653 A1 | 7/2011 | Ray et al. | |
| 2012/0059353 A1 | 3/2012 | Kovatchev et al. | |
| 2012/0245447 A1* | 9/2012 | Karan | G01N 33/48792 600/365 |
| 2013/0338629 A1 | 12/2013 | Agrawal et al. | |
| 2013/0338630 A1 | 12/2013 | Agrawal et al. | |
| 2014/0066892 A1 | 3/2014 | Keenan et al. | |
| 2014/0309615 A1 | 10/2014 | Mazlish | |
| 2014/0371682 A1 | 12/2014 | Bengtsson et al. | |
| 2015/0190098 A1 | 7/2015 | Patek et al. | |
| 2015/0347698 A1 | 12/2015 | Soni et al. | |
| 2016/0038673 A1 | 2/2016 | Morales | |
| 2016/0331310 A1 | 11/2016 | Kovatchev | |
| 2016/0342754 A1 | 11/2016 | Vettoretti et al. | |
| 2017/0053084 A1 | 2/2017 | McMahon et al. | |
| 2017/0296746 A1 | 10/2017 | Chen et al. | |
| 2018/0020988 A1 | 1/2018 | Patek | |
| 2018/0042559 A1 | 2/2018 | Cabrera, Jr. et al. | |
| 2018/0068581 A1 | 3/2018 | Skorheim et al. | |
| 2018/0085532 A1 | 3/2018 | Desborough et al. | |
| 2018/0353698 A1 | 12/2018 | Saint et al. | |
| 2019/0198148 A1 | 6/2019 | Aradottir et al. | |
| 2020/0205742 A1 | 7/2020 | Patek et al. | |
| 2020/0205743 A1 | 7/2020 | Patek et al. | |
| 2020/0205744 A1 | 7/2020 | Patek et al. | |
| 2021/0287775 A1 | 9/2021 | Aradottir et al. | |

FOREIGN PATENT DOCUMENTS

| | | |
|---|---|---|
| WO | 2004080401 A2 | 9/2004 |
| WO | 2013032965 A1 | 3/2013 |
| WO | 2016133879 A1 | 8/2016 |

OTHER PUBLICATIONS

Cobelli C., et al., "Modeling Glucose Metabolism in Man: Theory and Practice," Hormone and Metabolic Research, Supplement series, 1990, vol. 24, pp. 1-10.

Zisser H., et al., "Bolus Calculator: A Review of Four 'Smart' Insulin Pumps", Diabetes Technol Ther.,Dec. 2008 , vol. 10 (6), pp. 441-444.

Kovatchev et al., "Evaluation of a New Measure of Blood Glucose Variability in Diabetes", Diabetes Care, vol. 29(11), Nov. 2006, pp. 2433-2438.

Patek D.S., et al., "Empirical Representation of Blood Glucose Variability in a Compartmental Model", in Prediction Methods for Blood Glucose Concentration Springer, 2016, pp. 133-157.

* cited by examiner

EVALUATION AND VISUALIZATION OF GLYCEMIC DYSFUNCTION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. Ser. No. 16/721,810, filed Dec. 19, 2019, which is a continuation of U.S. application Ser. No. 16/721,679, filed Dec. 19, 2019, which claims priority to U.S. Provisional Patent Application No. 62/786,149, filed on Dec. 28, 2018. Each of the aforementioned applications is incorporated by reference herein in its entirety, and each is hereby expressly made a part of this specification.

BACKGROUND

With the growing adoption of CGM (continuous glucose monitoring) and connected devices, the availability and reliability of glucose time-series data has increased in recent years. However, despite the availability of reliable glucose data, accurate tracking of insulin and meal data and optimized and effective timing of meal time insulin bolusing continues to be problematic for many people with diabetes resulting in poor glucose control.

SUMMARY

An amount of glycemic dysfunction associated with mistiming (e.g., delay) of meal boluses based on replay analysis is determined. The amount of dysfunction of historical or estimated bolusing as compared to an optimally timed bolus based on the replay analysis is quantified and visualized. Inferences may be made about diabetes meal management regarding inputs from a patient.

According to an aspect, an estimated time, a user announced time, a reconciled estimated time, or a reconciled user announced time for a meal is compared to when the subject dosed insulin. Benefits (e.g., risk reduction) of insulin to an optimal dose and changing optimal pre-meal timing is evaluated.

In an implementation, a method of determining an amount of glycemic dysfunction is provided. The method comprises receiving continuous glucose monitoring (CGM) and insulin data pertaining to a subject, wherein the CGM and insulin data comprise an insulin bolus amount and a timing for the insulin bolus amount, performing a replay analysis on the CGM and insulin data, quantifying an amount of glycemic dysfunction using the replay analysis, and providing an output representative of the amount of glycemic dysfunction.

In an implementation, a system for determining an amount of glycemic dysfunction. The system comprises a data processor that receives continuous glucose monitoring (CGM) and insulin data pertaining to a subject, wherein the CGM and insulin data comprise an insulin bolus amount and a timing for the insulin bolus amount, a replay analyzer that generates a replay analysis using the CGM and insulin data, a quantifier that quantifies an amount of glycemic dysfunction using the replay analysis, and an output device that provides an output representative of the amount of glycemic dysfunction.

In an implementation, a method of determining an amount of glycemic dysfunction is provided. The method comprises receiving historical blood glucose (BG) data and historical insulin data at a replay analyzer, performing a plurality of replay analyses for historical boluses and for estimated meals using the historical BG data and the historical insulin data, performing at least one insulin on board (IOB) data analysis using at least one of the plurality of replay analyses, performing at least one BG data analysis using at least one of the plurality of replay analyses, performing at least one discrepancy analysis and at least one comparison using the at least one IOB data analysis and the at least one BG data analysis, and providing an output based on the at least one discrepancy analysis and the at least one comparison.

In an implementation, a system for determining an amount of glycemic dysfunction. The system comprises an input device configured to receive blood glucose (BG) data, insulin data, and a plurality of functions, a replay analyzer configured to receive the BG data, the insulin data, and the plurality of functions, and perform a plurality of replay analyses for historical boluses and for estimated meals using the BG data, the insulin data, and the plurality of functions, an insulin on board (IOB) assessor configured to perform a plurality of IOB assessments using at least one of the insulin data or the plurality of replay analyses, a BG risk profiler configured to perform a plurality of BG risk profiles using at least one of the BG data or the plurality of replay analyses, an IOB profiler configured to perform a plurality of IOB profiles using at least one of the plurality of IOB assessments, a BG risk comparator configured to determine at least one of a risk profile plot or a BG risk score using the output of the BG risk profiler, a discrepancy analyzer configured to perform a plurality of discrepancy analyses using the IOB profiles and the IOB assessments to determine at least one of an IOB profile plot, an IOB discrepancy plot, or an IOB trace similarity score, and an output device configured to output at least one of the risk profile plot, the BG risk score, the IOB profile plot, the IOB discrepancy plot, or the IOB trace similarity score.

In an implementation, a method of providing a recommendation based on glycemic risk is provided. The method comprises receiving at least one of historical blood glucose (BG) data or historical insulin data for a subject, wherein the BG data and insulin data comprise an insulin bolus amount and a timing for the insulin bolus amount, determining a first risk score for glycemic dysfunction for the subject based on the at least one of the historical BG data or the historical insulin data, receiving at least one of optimal BG data or optimal insulin data for the subject, determining a second risk score for glycemic dysfunction for the subject based on the at least one of the optimal BG data or the optimal insulin data, comparing the first risk score with the second risk score, and outputting a recommendation based on the comparison of the first risk score with the second risk score.

In an implementation, a method of evaluating glycemic risk is provided. The method comprises determining a historical risk score for glycemic dysfunction based on at least one of historical blood glucose (BG) data or historical insulin data, wherein the historical BG data and historical insulin data comprise an insulin bolus amount and a timing for the insulin bolus amount, determining an optimal risk score for glycemic dysfunction based on at least one of optimal BG data or optimal insulin data, determining a difference between the historical risk score and the optimal risk score, and providing a recommendation based on the difference and based on a threshold In an implementation, a method comprises computing a first IOB trace based on a record of actual boluses, computing a second IOB trace of optimal treatments, comparing the first IOB trace with the second IOB trace to determine an IOB similarity score, and using the IOB similarity score to change at least one of smart alert behavior, user recommendations, report features, and visualizations.

In an implementation, a system comprises a discrepancy analyzer configured to determine an IOB similarity score using a comparison of a first IOB trace based on a record of actual boluses and a second IOB trace of optimal treatments; and an output device configured to output the IOB similarity score.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
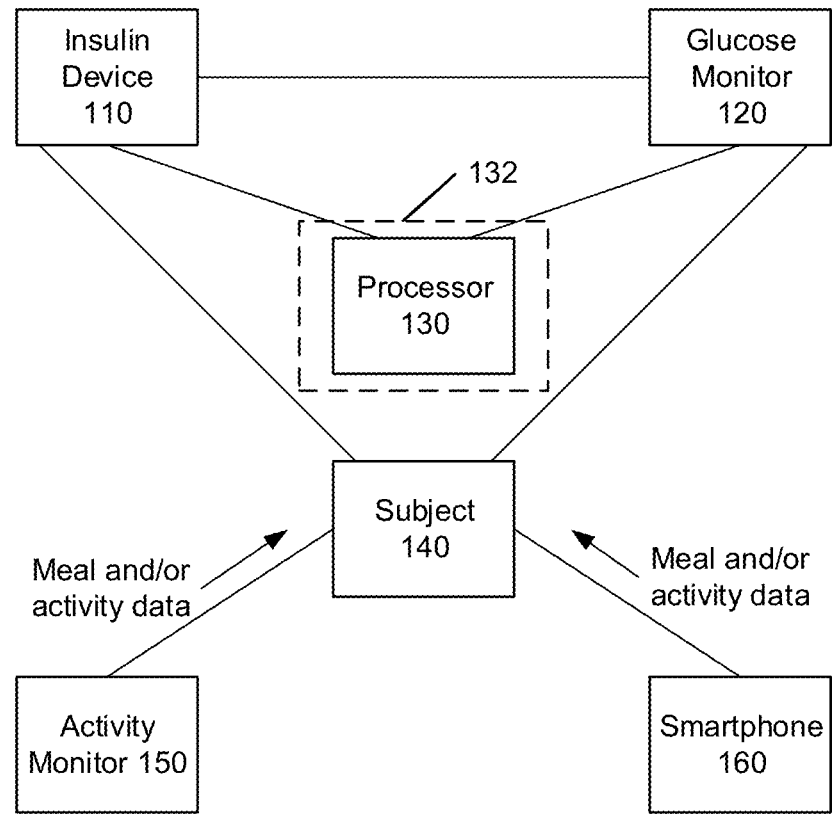
FIG. 1 is a high level functional block diagram of an embodiment of the invention.

The claimed subject matter is described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The invention is intended for replay use, meaning that the impact of inefficient or suboptimal bolus in the subject's own historical data can be illustrated in terms of glycemic risk or insulin delivery profiles relative to optimal bolusing in the same data set. A replay bolus timing effect is determined. Pre-meal bolus compliance is determined. Implementations of the invention seek to quantify in a specific way the effects of misinformation about meals (both in terms of timing and composition). The benefits (e.g., risk reduction) of insulin is evaluated with respect to an optimal dose and with respect to changing optimal pre-meal timing. Meals can be any length of time, depending on the implementation. A meal may be an event having a length of time or an event spanning a window of time. The window of time may be any duration or length of time, depending on the implementation. In some implementations, the length of time or window of time may vary from meal to meal or may be a fixed duration. It should be appreciated by one skilled in the art that a meal is a window of time, and that window of time can be defined in a variety of different ways.

As described further herein, an amount of glycemic dysfunction associated with mis-timing (e.g., delay) of meal boluses of a subject is determined based on replay analysis and then the amount of dysfunction of historical or estimated bolusing as compared to an optimally timed bolus based on the replay analysis may be quantified and may be output in a visual form for a subject or a user. Inferences about diabetes meal management may be made using inputs provided by the subject or the user. Using historical and replay meal bolus reconciliation, two categories for diabetes management improvement may be distinguished: mis-timed boluses and missing meal boluses.

Aspects described herein address the problem of identifying patterns and glycemic impacts of both inefficient bolus doses and mis-timed boluses in a patient (also referred to herein as a subject) with diabetes. The problem is complicated by the fact that the patient's perception of bolus efficiency and/or appropriateness of timing is determined by the consistency with which they execute prescribed insulin self-treatment guidelines. For example, under physician guidance to bolus at or just before mealtime, a patient may generally believe that they are already deriving maximal benefit from insulin therapy when they execute this strategy for only two out of three meals a day when in fact late bolusing for the third meal may be contributing disproportionately to glycemic dysfunction in the form of exposure to hypoglycemia or hyperglycemia. Vague recollection of "compliant behavior" is often far from an accurate assessment from exhaustive analysis of retrospective data. Consequently, neither the patient nor the patient's caregivers are able to develop a clear understanding of the existence of inefficient insulin therapy, or of the impact of inefficient therapy, from conventional methods involving subjective recall or partially complete data records.

Implementations described herein provide a technically nontrivial solution by means of (i) exhaustive analysis of blood glucose records, associated records of insulin data, and possibly other metabolically relevant information, to (ii) the assessment of a sequence of meal events (comprising carbohydrates, fat, and protein content) from announced or inferred meals aligned to the blood glucose and insulin records, (iii) the derivation of a mechanism by which the glycemic impact of alternative dosing can be estimated in the historical record, (iv) applying this mechanism systematically to determine the glycemic impact of numerically optimal dosing at times of historical boluses and also at times of validated meal events, including performing replay simulations at times of historical boluses or at times in advance of estimated meals, (v) quantifying in an aggregate sense the glycemic dysfunction associated with inefficient insulin delivery, including impacts in terms of risk of exposure to hypoglycemia and hyperglycemia, (vi) accounting for the systematic discrepancies in insulin delivery between historical bolusing and numerically optimal bolusing, including an overall similarity score between optimal bolusing and historical patterns of insulin delivery and also the identification of times of the day where on average historical insulin delivery deviates from numerically optimal insulin delivery.

Advantages over previously existing self-assessment or clinical tools are provided. The systems and methods described herein are systematic, accounting for all available blood glucose and insulin data, which easily overwhelms "pencil and paper" analysis and even "spreadsheet" analysis with standard statistical assessment. The systems and methods are comprehensive in that they identify complex relationships correlations between blood glucose, insulin, and meal records, through the lens of a patient-specific mathematical model. As such, patterns of inefficient bolusing and of glycemic dysfunction emerge from statistical analysis of these patient-specific interactions. The systems and methods described herein are immune to cognitive biases that are introduced by (i) the patient in recalling insulin delivery and/or meal events or (ii) by the physician in framing questions about the patient's experience that lead to a misleading understanding of the patient's therapeutic routine.

Various calculation metrics may be used depending on the implementation, including for example, but not limited to, hg_min which is the minimum level of historical glycemic dysfunction required (could be measured as BG risk, time in range, mean, etc., and may be broken out by time of day in hours, minutes, or other useful increments), gdiff_min which is the minimum level of improvement of glycemic outcomes as measured by difference between historical and simulated glucose derived metrics, and idiff_min which is the minimum level of normalized change in insulin therapy required for improved outcomes (could be frequency based and/or magnitude based).

FIG. 1 is a high level functional block diagram 100 of an embodiment of the invention. A processor 130 communicates with an insulin device 110 and a glucose monitor 120.

The insulin device 110 and the glucose monitor 120 communicate with a subject 140 to deliver insulin to the subject 140 and monitor glucose levels of the subject 140, respectively. The processor 130 is configured to perform the calculations described further herein. The insulin device 110 and the glucose monitor 120 may be implemented as separate devices or as a single device, within a single device, or across multiple devices. The processor 130 can be implemented locally in the insulin device 110, the glucose monitor 120, or as standalone device shown dashed lines as standalone device 132 (or in any combination of two or more of the insulin device 110, the glucose monitor 120, or a standalone device). The processor 130 or a portion of the system can be located remotely such as within a server or a cloud-based system.

Examples of insulin devices, such as the insulin device 110, include insulin syringes, external pumps, and patch pumps that deliver insulin to a subject, typically into the subcutaneous tissue. Insulin devices 110 also includes devices that deliver insulin by different means, such as insulin inhalers, insulin jet injectors, intravenous infusion pumps, and implantable insulin pumps. In some embodiments, a subject will use two or more insulin delivery devices in combination, for example injecting long-acting insulin with a syringe and using inhaled insulin before meals. In other embodiments, these devices can deliver other drugs that help control glucose levels such as glucagon, pramlintide, or glucose-like peptide-1 (GLP 1).

Examples of a glucose monitor, such as the glucose monitor 120, include continuous glucose monitors that record glucose values at regular intervals, e.g., 1, 5, or 10 minutes, etc. These continuous glucose monitors can use, for example, electrochemical or optical sensors that are inserted transcutaneously, wholly implanted, or measure tissue non-invasively. Examples of a glucose monitor, such as the glucose monitor 120, also include devices that draw blood or other fluids periodically to measure glucose, such as intravenous blood glucose monitors, microperfusion sampling, or periodic finger sticks. In some embodiments, the glucose readings are provided in near realtime. In other embodiments, the glucose reading determined by the glucose monitor can be stored on the glucose monitor itself for subsequent retrieval.

Figure 21:
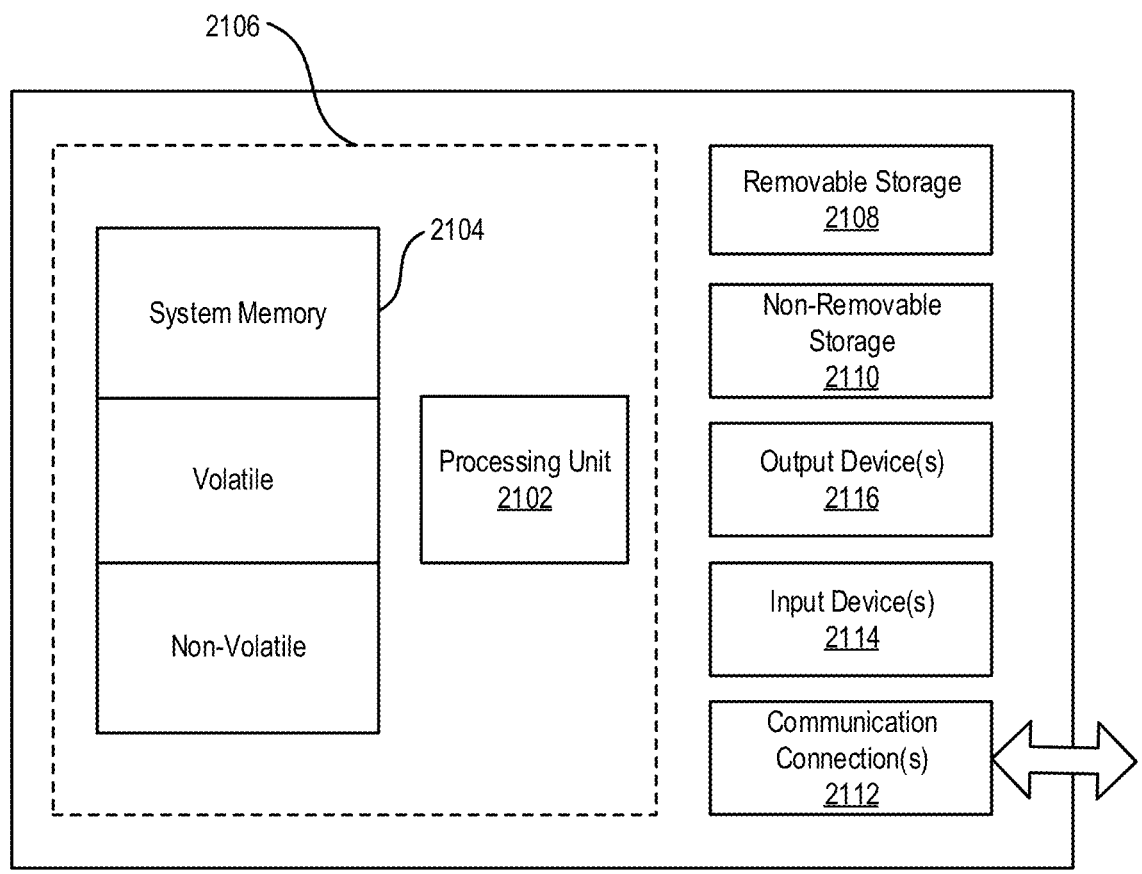
FIG. 21 shows an exemplary computing environment in which example embodiments and aspects may be implemented.

The insulin device 110, the glucose monitor 120, and the standalone device 132 may be implemented using a variety of computing devices such as smartphones, desktop computers, laptop computers, and tablets. Other types of computing devices may be supported. A suitable computing device is illustrated in FIG. 21 as the computing device 2100 and cloud-based applications.

The insulin device 110, the glucose monitor 120, and the standalone device 132 may be in communication through a network. The network may be a variety of network types including the public switched telephone network (PSTN), a cellular telephone network, and a packet switched network (e.g., the Internet). Although only one insulin device 110, one glucose monitor 120, and one processor 130 (within one standalone device 132) are shown in FIG. 1, there is no limit to the number of insulin devices, glucose monitors, processors, and stand alone devices that may be supported. An activity monitor 150 and/or a smartphone 160 may also be used to collect meal and/or activity data from or pertaining to the subject 140, and provide the meal and/or activity data to the processor 130.

The processor 130 may execute an operating system and one or more applications. The operating system may control which applications are executed by the insulin device 110, the glucose monitor 120, and the standalone device 132, as well as control how the applications interact with one or more sensors, services, or other resources of the insulin device 110, the glucose monitor 120, and the standalone device 132.

The processor 130 receives data from the insulin device 110 and the glucose monitor 120, as well as from the subject 140 in some implementations, and performs a replay analysis that evaluates the patient's current meal bolusing strategy and compares it to alternative bolusing times and insulin amounts.

Figure 2:
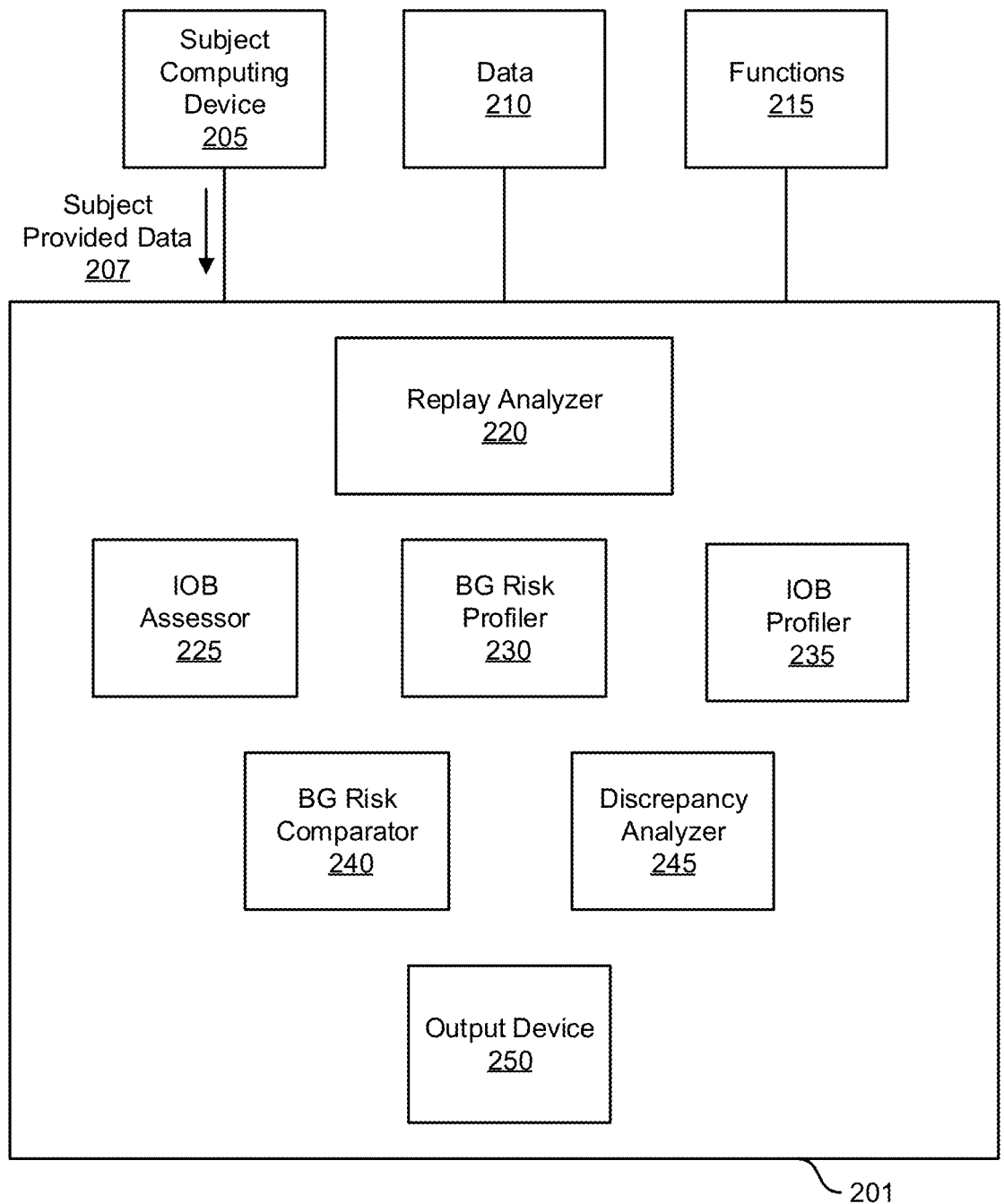
FIG. 2 is an illustration of an exemplary environment for evaluating and visualizing glycemic dysfunction.

More particularly, FIG. 2 is an illustration of an exemplary environment 200 for evaluating and visualizing glycemic dysfunction. A computing device 201 comprises one or more processors, such as the processor 130, that may implement a replay analyzer 220, an insulin on board (IOB) assessor 225, a blood glucose (BG) profiler 230, an IOB profiler 235, a BG risk comparator 240, a discrepancy analyzer 245, and an output device 250. The computing device 201 may be implemented in a computing device illustrated in FIG. 21 as the computing device 2100, and can also be implemented on a microcontroller or using a processor that is located in the insulin device 110, the glucose monitor 120, or other insulin delivery device, or as a standalone component (or a combination of two or more of insulin device 110, the glucose monitor 120, or other insulin delivery device, or standalone component).

The computing device 201 is in communication with a subject computing device 205 e.g., via a network and/or communications interface, and is configured to receive data 210 and functions 215 from one or more devices or processors via a network and/or communications interface, such as the insulin device 110 and the glucose monitor 120, as well as those maintained by or associated with physicians, caregivers, healthcare providers, hospitals, clinics, universities, etc.

The subject computing device 205 (such as the activity monitor 150, the smartphone 160, or any other type of computing device such as the computing device 2100 described with respect to FIG. 21) may be used by the subject 140 to input data (subject provided data 207) about the subject's meals and bolusing (e.g., timing, amounts, etc.). In some implementations, this data may be considered to be untrusted data because it is subject to human error, bias, and/or behavior inconsistencies or anomalies. The data 210 may comprise data that is not subject provided data 207 such as historic blood glucose amounts, historic insulin dosage amounts, meal information, initial (e.g., pre-meal) state of the subject, insulin dosing strategy, etc. In some implementations, this data may be considered to be trusted data because it is machine provided, machine verified, has been determined to have a confidence value exceeding a predetermined threshold, and/or is immune from, resistant to, and/or uninfluenced by human error, bias, or behavior inconsistencies or anomalies. The functions 215 may comprise one or more metabolic modeling functions, such as a meal compiler (e.g., the meal compiler 303) and a replay compiler (e.g., the replay compiler 304), which produces a replay predictive function (e.g., the replay predictive function 305) as well as one or more risk, profiling, and assessment functions as described further herein.

The replay analyzer 220 uses the subject provided data 207, the data 210, and the functions 215 to perform one or more replay analyses, such as a replay with optimal boluses at times of historical boluses, and a replay with optimal boluses at times of assessed meals, as described further herein. Depending on the implementation, one or more of the outputs from the replay analyzer 220 may be provided to one or more of the IOB assessor 225, the BG risk profiler 230, and the IOB profiler 235. In this manner, in an implementation, the replay analyzer 220 may act as a data processor that receives CGM and insulin data pertaining to a subject. In some implementations, alternatively or additionally, the replay analyzer 220 may act as a data generator that generates CGM and insulin data pertaining to a subject.

The IOB assessor 225 may perform one or more IOB assessments, such as IOB assessment for historical data, IOB assessment for optimal boluses at historical times, and IOB assessment for optimal boluses at estimated meal times. Depending on the implementation, one or more of the outputs from the IOB assessor 225 may be provided to one or more of the IOB profiler 235 and the discrepancy analyzer 245.

The BG risk profiler 230 may generate one or more BG risk profiles, such as BG risk profiling for optimal boluses at historical times, and BG risk profiling for optimal boluses at estimated meal times. Depending on the implementation, one or more of the outputs from the BG risk profiler 230 may be provided to one or more of the BG risk comparator 240 and the discrepancy analyzer 245. In this manner, in an implementation, the BG risk profiler 230 acts as a quantifier that quantifies an amount of glycemic dysfunction using the replay analysis.

The IOB profiler 235 may generate one or more IOB profiles, such as IOB profiling for optimal boluses at historical times, and IOB profiling for optimal boluses at estimated meal times. Depending on the implementation, one or more of the outputs from the IOB profiler 235 may be provided to the discrepancy analyzer 245.

The BG risk comparator 240 performs a BG risk profile comparison function to generate risk profile plots and total BG risk scores, which may be stored, displayed, and/or transmitted by the output device 250.

The discrepancy analyzer 245 may perform one or more IOB discrepancy analyses and provide one or more of plots and scores to the output device 250 for storage, display, and/or transmission.

Figure 3A:
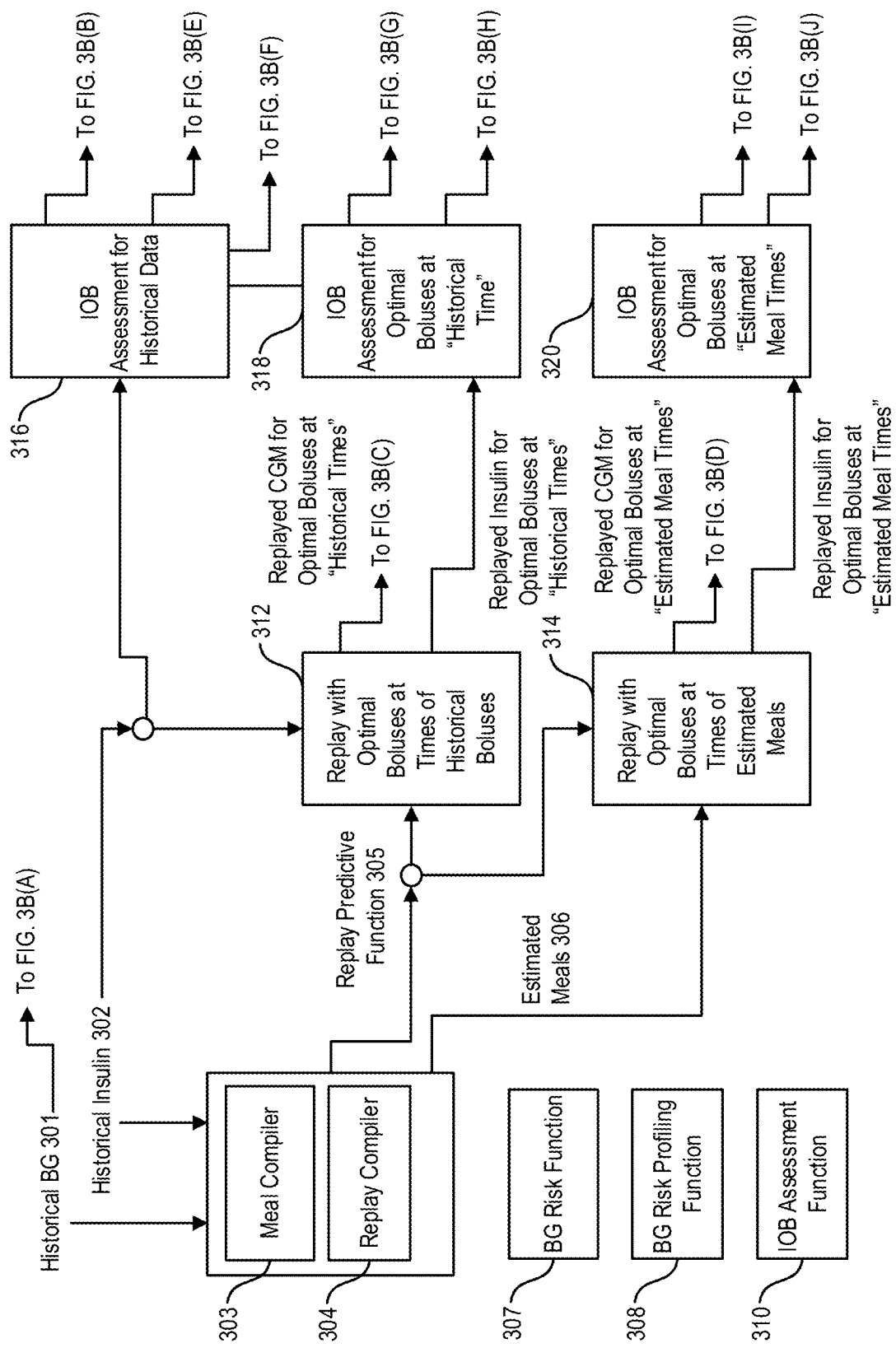
FIGS. 3A and 3B show a schematic block diagram of an implementation of an exemplary system with related methods for evaluating and visualizing glycemic dysfunction.
Figure 3B:
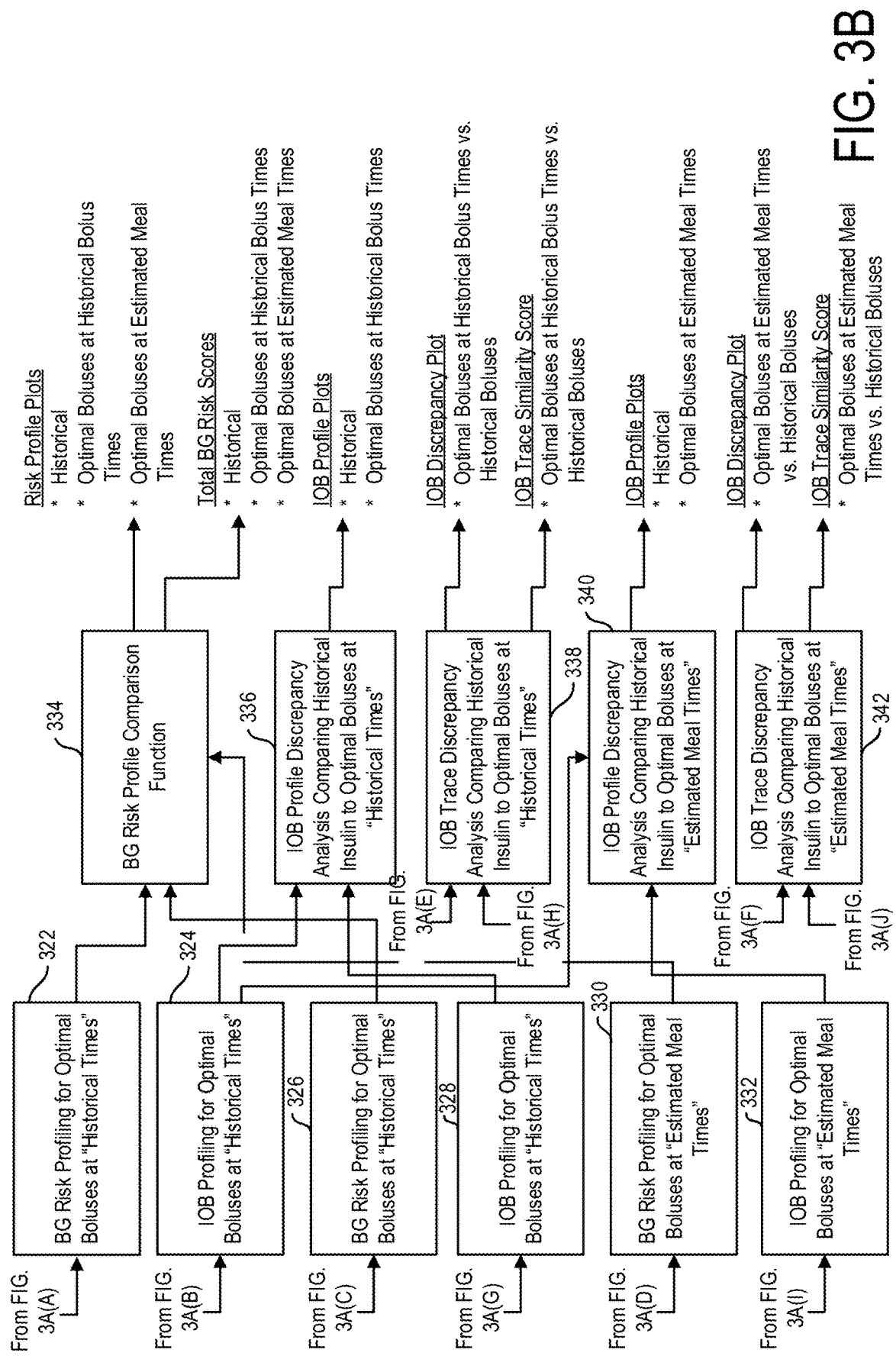

FIGS. 3A and 3B show a schematic block diagram of an implementation of an exemplary system 300 with related methods for evaluating and visualizing glycemic dysfunction. The system is directed to a replay analysis tool that evaluates a subject's current meal bolusing strategy and compares it to alternative bolusing times and insulin amounts.

Outputs of the system 300 may be used to identify behavioral issues, e.g., by isolating the impact of timing, carb counting, and carb ratio of a bolus with respect to meals of the subject. Replay simulation analysis may be used to assess the impact of numerically optimal (remove inaccurate carb counts or inappropriate carb ratios) boluses at historical bolus times, and to assess the impact of numerically optimal boluses at estimated historical meal times.

In an implementation, when the replay simulator determines that it is time to compute a numerically optimal bolus, it generates a set of candidate boluses, simulates future BG values associated with each candidate bolus, uses a risk analysis, such as a velocity dependent risk analysis, to "score" the simulated BG trajectory for each candidate bolus, and picks and implements the best bolus and continues to replay simulate until the time of the next bolus. Candidate boluses via replay may be replayed at a time within a targeted window of time surrounding a reconciled meal time or historical dose time, in addition to, or alternative to, replaying at those exact times.

The system 300 uses accurate assessment of both timing and amount of meals in the historical data. Inputs comprising the data 210 (e.g., received from storage) and/or the subject provided data 207 from the subject computing device 205 are directed to CGM (continuous glucose monitoring) data and insulin data, including insulin bolus amount and timing. In an implementation, the historical BG data 301 (represented by $\{bg(t)\}_{t=0, 1} \ldots$) and the historical insulin 302 (represented by $\{i(t)\}_{t=0, 1} \ldots$) are time-series and used as inputs. It is noted that this is original data.

Undocumented meal times are estimated using CGM data (e.g., the historical BG data 301) and insulin data (e.g., the historical insulin data 302), and possibly also user acknowledgements of meals, to estimate times and amounts of all carb events. Other inputs that may be used in other implementations include exercise (e.g., to determine how to optimize treatment around exercise), rescue carbs (e.g., to determine the amount required), other meal bolusing strategies (e.g., split, delayed, and extended boluses), and Type 2 treatments including oral medications etc. This data may be trusted or untrusted.

In an implementation, the CGM data and the insulin data is "discretized" in time (e.g., snapped to the nearest 5-minute sample) and aggregated appropriately. For example, if there was more than one bolus in a five-minute interval, then the insulin value for the corresponding sample would be the sum of the boluses (plus the impact of basal). This CGM data and insulin data forms the basic input for replay state estimation, which in turn is a step to constructing the replay simulator for that data set.

The historical BG data 301 and the historical insulin data 302 are provided to a meal compiler 303 and a replay compiler 304, which in turn output a replay predictive function 305 and an assessed sequence of estimated meals 306. The replay predictive function 305 provides the ability to predict blood glucose outcomes that would have been associated with alternative insulin delivery (i.e., deviating from historical insulin delivery) from any point in the historical record. Specifically, it maps an alternative insulin time series 302 (which could be represented by $\{i_{alt}(t)\}_{t=0, 1} \ldots$) to a predicted time-series of blood glucose data (which could be represented by $\{bg_{alt}(t)\}_{t=0, 1} \ldots$).

The meal compiler 303 analyzes historical BG data and insulin delivery data, and possibly other sources of historical data including logged and/or recalled meal events directly from the patient. The outputted sequence of estimated meals 306 is represents a reconciliation between (i) meal events that can be detected/estimated from correlations between the historical blood glucose and insulin delivery data and (ii) meal events that are inferred or directly recalled from other sources of data. Detected/estimated meals from historical blood glucose and insulin data can be derived from a variety of mechanisms, including deconvolution or regularized deconvolution (see e.g., Patek S. D. et al., "Empirical Representation of Blood Glucose Variability in a Compartmental Model," in Kirchsteiger H. et al. (eds) *Prediction Methods for Blood Glucose Concentration* (Lecture Notes in Bioengineering), 2016.)

Meal times can also be estimated from the same data set using other approaches known to one skilled in the art of metabolic models. A metabolic model describes the whole-body and regional glucose metabolism (see e.g., Cobelli C. et al., "Modeling Glucose Metabolism in Man: Theory and Practice", Hormone and Metabolic Research, Supplemental Series, 1990, 24: 1-10, https://www.ncbi.nlm.nih.gov/pubmed/2272612.) These models describe: levels and distribution of glucose and other metabolites in different compartments of the body, levels and distribution of insulin and other hormones and drugs in different compartments of the body, and glucose transport kinetics between compartments that describe consumption and production. These models can be used in clinical settings where compartmental inputs and outputs are tracked by drawing samples (e.g., venous blood or interstitial fluid) and using clinical analyzers. There are also tracer studies track the distribution of metabolites. In these studies, the inputs (such as meals, insulin and exercise) and outputs are carefully controlled and measured. The resulting metabolic model can provide a patient-specific model of glucose excursion from a meal that can be compared with a patient glucose monitor to estimate meal properties.

There are also methods to detect the timing and magnitude of meal excursions from patterns and features in the glucose monitor traces. Examples include detecting acceleration or upward changes in the CGM data or fitting a meal excursion model (e.g., minimal model) to the time series. Meal information could also be obtained directly from a clinical study or patient records. Reconciliation between detected/estimated meals and uncertain or untrustworthy sources of meal data can be achieved for example by clustering detected and reported meals and averaging meal content. The assessed sequence of estimated meals 306 is determined and output from the compilers 303, 304.

In an implementation, the meal compiler 303 estimates the meal time and/or effective size from historic blood glucose measurements (e.g., CGM), insulin doses (e.g., pump or pen), and optionally meal announcements.

The replay compiler 304 also analyzes historical BG and insulin delivery data, and possibly other sources of historical data including logged and/or recalled meal events directly from the patient. It produces a mathematical function, a replay predictive function 305, that can be expressed in a variety of ways (including as a computer algorithm) that provides the ability to predict blood glucose outcomes that would have been associated with alternative insulin delivery (i.e. deviating from historical insulin delivery) from any point in the historical record. The replay predictive function 305 evaluates if other insulin dosing strategies for the same meal would have better outcomes (e.g., lower glycemic risk). The replay predictive function 305 takes the initial (pre-meal) state of the patient, one or more meal events, and an insulin dosing strategy as inputs and then maps it to the resulting glucose excursions for that meal/day. The functionality of the replay predictive function can be derived from blood glucose data by inserting the validated stream of estimated meals into the mathematical model from which they are derived (see e.g., Patek S. D. et al., "Empirical Representation of Blood Glucose Variability in a Compartmental Model," in Kirchsteiger H. et al. (eds) *Prediction Methods for Blood Glucose Concentration* (Lecture Notes in Bioengineering), 2016). Alternatively, other blood glucose simulation methodologies may be applied to the validated sequence of estimated meals, including simulators derived from compartmental models or from data-driven methods.

The historical BG 301 may also be provided to a BG risk profiler (such as the BG risk profiler 230) for use in the determination of BG risk profiling for optimal boluses at historical times 322. The historical insulin 302 may also be provided to an IOB assessor (such as the IOB assessor 225) for use in the determination of IOB assessment for historical data 316, and also to a replay analyzer (such as the replay analyzer 220) for use in the replay with optimal boluses at times of historical boluses 312.

Other functions that may be used by the system 300 include a BG risk function 307 used to identify numerically optimal boluses to be inserted into the replay predictive function 305 either at times of historical boluses or at times of validated meal events, a BG risk profiling function 308 used to derived an aggregated assessment of risk of hypoglycemia and hyperglycemia exposure either in the historical blood glucose record or in replayed glucose records from the replay predictive function, and an IOB assessment function 310.

The IOB assessment function 310 is a calculation that tracks how much insulin is still present in the body from previous doses that includes the time course of injected insulin acting in the body, including how insulin is absorbed, starts acting on glucose levels, and clears the body. For example, a fast-acting insulin might reach a peak action at one hours with a total duration of action of 4 hours. The IOB function can take a variety of mathematical forms to describe how long it takes insulin to reach its peak value and the decay curve that follows. These IOB functions are used in bolus calculators (on insulin pumps and phone apps) that help diabetic subjects estimates bolus insulin doses (see e.g., Zisser H. et al., "Bolus Calculator: A Review of Four 'Smart' Insulin Pumps", Diabetes Technology & Therapeutics, 2008 December; 10(6): 441-4, doi: 10.1089/dia.2007.0284, https://www.ncbi.nlm.nih.gov/pubmed/19049372. In some embodiments, the IOB function uses parameters provided by the patient, their healthcare provider, or the insulin manufacture. In other embodiments, the IOB assessment function can be optimized to create a patient-specific insulin action curve.

In an implementation, the replay predictive function 305 maps the original data (e.g., meal and insulin) to the observations (e.g., CGM) with a sufficient degree of accuracy, maps alternate dosing strategies to the resulting glucose excursions in a manner that models the patient's physiology (e.g., insulin activity and carbohydrate sensitivity), and provides reliable and interpretable solutions to the problem such as an estimate of IOB that is a stable and smooth functions.

In an implementation, known inputs and user-announced meals are used to generate a function that can replay alternate insulin strategies with the same inputs states. This is a construct where a function takes input data, extracts knowledge, and creates a new function.

The replay predictive function 305 could also be constructed from the same dataset using other approaches known to one skilled in the art of metabolic models. One example approach would be to fit the parameters of a metabolic model to the subject's data or a clinical study. Another possible approach would be to train a neural network with similar data to predict the glucose excursions.

Regarding the system 300 with respect to elements 312-342, in view of a behavior issue such as a missed meal or incorrect user entry for example, the system determines and quantifies the glycemic dysfunction associated with improper timing of boluses associated with meals based on the CGM and insulin data. This may be used to identify behavioral issues, and to isolate the impact of timing and carb counting and carb ratios of a bolus with respect to meals, as described further herein, e.g., with respect to FIGS. 4-15B.

At 312, replay with optimal boluses at times of historical boluses is performed (e.g., by the replay analyzer 220) using the replay predictive function 305 and the historical insulin 302 as inputs. The output of 312 comprises replayed CGM for optimal boluses at historical times and replayed insulin for optimal boluses at historical times.

At 314, replay with optimal boluses at times of estimated meals is performed (e.g., by the replay analyzer 220) using the replay predictive function 305 and the estimated meals data 306 as inputs. The output of 314 comprises replayed CGM for optimal boluses at estimated meal times and replayed insulin for optimal boluses at estimated meal times. It is noted that the outputs of 312 and 314 are simulated data using replay. This simulates how risks, IOB, BG, and related data and results would have been different if the subject had bolused at these times.

At 316, an IOB assessment for historical data is performed (e.g., by the IOB assessor 225) using the historical insulin 302 as input. Any known technique for performing an IOB assessment may be used. The output of 316 is used in IOB profiling for optimal boluses at historical times at 324, and at 338 and 342 described further below.

At 318, an IOB assessment for optimal boluses at historical times is performed (e.g., by the IOB assessor 225) using the replayed insulin for optimal boluses at historical times from 312 as input. The output of 318 is used in IOB profiling for optimal boluses at historical times at 328, and at 338 described further below.

At 320, an IOB assessment for optimal boluses at estimated meal times is performed (e.g., by the IOB assessor 225) using the replayed insulin for optimal boluses at estimated meal times as input. The output of 320 is used in IOB profiling for optimal boluses at estimated meal times at 332, and at 342 described further below.

At 322, BG risk profiling for optimal boluses at historical times is performed (e.g., by the BG risk profiler 230) using the historical BG 301 as input. The output is used by a BG risk profile comparison function 334 described further below.

As noted above, at 324, IOB profiling for optimal boluses at historical times is performed (e.g., by the IOB profiler 235). The output of 324 is used at 336 and 340 described further below.

At 326, BG risk profiling for optimal boluses at historical times is performed (e.g., by the BG risk profiler 230) using the replayed CGM for optimal boluses at historical times that was generated at 312. The output of 326 is used at 334 described further below.

At 328, IOB profiling for optimal boluses at historical times is performed (e.g., by the IOB profiler 235) using as input the output of the IOB assessment for optimal boluses at historical times 318. The output of 328 is used at 336 described further below.

At 330, BG risk profiling for optimal boluses at estimated meal times is performed (e.g., by the BG risk profiler 230) using the replayed CGM for optimal boluses at estimated meal times that was generated at 314. The output of 330 is used at 334 described further below.

At 332, IOB profiling for optimal boluses at estimated meal times is performed (e.g., by the IOB profiler 235) using as input the output of the IOB assessment for optimal boluses at estimated meal times 320. The output of 332 is used at 340 described further below.

Regarding outputs, charts and/or reports may be generated, transmitted, and/or displayed to show how better results for the subject could have been achieved if the patient did not have a behavior issue. In some implementations, the methods and systems contemplated herein determine whether or not to display certain recommendations, or certain graphical inferences, or perform other actions based on thresholds described further herein.

A BG risk profile comparison is performed (e.g., by the BG risk comparator 240) using a BG risk profile comparison function 334 that receives as input the outputs of the BG risk profile for optimal boluses at historical times of 322 and 326 and the BG risk profile for optimal boluses at estimate meal times of 330. The output of the BG risk profile comparison function 334 may comprise risk profile plots and total BG risk scores, each with data and/or indicators directed to historical information, optimal boluses at historical bolus times information, and optimal boluses at estimated meal times information, such as those described further herein with respect to FIGS. 4-15B for example.

The differential of comparative BG risk profiles can be quantified to produce numerical output for a variety of uses and/or a feedback loop, including historical CGM, replay-simulated CGM with numerically optimal boluses at historical bolus times, and replay-simulated CGM with numerically optimal boluses inserted at estimated meal times.

Figure 4:
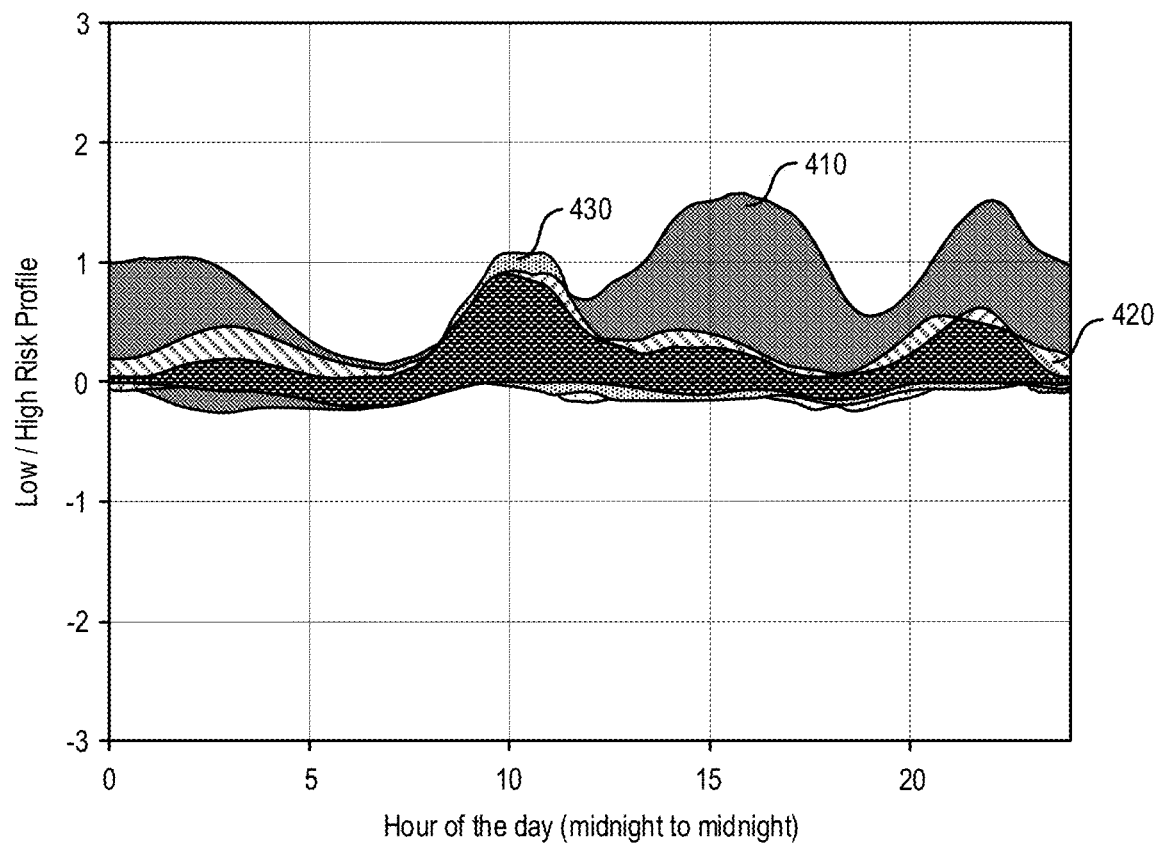
FIG. 4 is an illustration of various risk profile plots according to an example.

Differentials of comparative BG risk profiles may be quantified in various ways such as using plots and visualizations, and using risk indices that indicate high blood glucose risk, low glucose risk, or total glycemic risk, for example, as well as indicating the number and extent of excursions into an out-of-range BG level, such as those described with respect to FIG. 4, for example.

At 336, an IOB profile discrepancy analysis is performed (e.g., by the discrepancy analyzer 245) comparing historical insulin to optimal boluses at historical times. The input to 336 comprises the output of the IOB profiling for optimal boluses at historical times of 324 and 328, and the output of 336 comprises IOB profile plots with data and/or indicators directed to historical information and optimal boluses at historical bolus times information.

At 338, an IOB trace discrepancy analysis is performed (e.g., by the discrepancy analyzer 245) comparing historical insulin to optimal boluses at historical times. The input to 338 comprises the output of the IOB assessment for historical data of 316 and the output of the IOB assessment for optimal boluses at historical times of 318. The output of 338 comprises IOB discrepancy plots and IOB trace similarity scores with data and/or indicators directed to optimal boluses at historical bolus times vs. historical boluses information.

At 340, an IOB profile discrepancy analysis is performed (e.g., by the discrepancy analyzer 245) comparing historical insulin to optimal boluses at estimated meal times. The input to 340 comprises the output of the IOB profiling for optimal boluses at historical times of 324 and the output of the IOB profiling for optimal boluses at estimated meal times of 332. The output of 340 comprises IOB profile plots with data and/or indicators directed to historical information and optimal boluses at estimated meal times information.

At 342, an IOB trace discrepancy analysis is performed (e.g., by the discrepancy analyzer 245) comparing historical insulin to optimal boluses at estimated meal times. The input to 342 comprises the output of the IOB assessment for historical data of 316 and the output of the IOB assessment for optimal boluses at estimated meal times of 320. The output of 342 comprises IOB discrepancy plots and IOB trace similarity scores with data and/or indicators directed to optimal boluses at estimated meal times vs. historical boluses information.

Thus, the replay simulation output shows glycemic dysfunction at historical times. For example, historical/estimated risk profiles on a graph can show difference in glycemic exposure. Historical CGM may be shown vs. replay-simulated CGM with optimal boluses at historical bolus times, and vs. replay-simulated CGM with optimal boluses at estimated meal times and historical bolus times.

Risk indices may be shown, such as high blood glucose risk, low blood glucose risk, and total glycemic risk. These risks may be displayed as representations on a chart with numbers, colors, quantified values, etc. The number and extent of excursion into the out-of-range BG levels may also be identified and indicated. It is contemplated that a numerical representation may be used to indicate glycemic function/goodness, such as a comparison between two numbers, good vs. bad.

Another output may be an indication of compliance with the pre-meal bolusing requirement. A subject's ideal pre-meal bolus is determined, and then the subject's deviation from this ideal pre-meal bolus is determined. A score may be generated and outputted, e.g., numerically, on a chart, etc. In this embodiment, the step of quantifying a glycemic dysfunction can be viewed as quantifying compliance with (or deviation from) ideal pre-meal bolus timing. In an implementation, a visualization (showing effects of compliance) or a recommendation (e.g., "bolus 20 minutes before this type of meal in the future") may be generated and outputted.

The various outputs described herein could be used as a risk stratification tool for health care professionals to identify subjects by pre-meal bolusing compliance and the potential benefits of therapy adjustments. The outputs could be used to highlight the most impactful potential changes in a clarity report (e.g., changing insulin timing versus bolus amounts or highlight best meals). The outputs could be used to trigger coaching comments and discussion points via coaching call or chatbot prompts.

FIG. 4 is an illustration of various risk profile plots 400 according to an example. In this example, for a subject, the total risk CGM is 0.99, the total risk with optimal bolusing at historical bolus times is 0.46, the total risk with optimal bolusing at estimated meal times is 0.39, the IOB trace similarity score against optimal boluses at historical bolus times is 0.69, and the IOB trace similarity score against optimal boluses at estimated meal times is 0.59. The number of days in the sample was 13 days.

Total risk CGM is a value that captures both hyperglycemia and hypoglycemia risk over a time segment as a single value. Any known technique for determining the value may be used. In an implementation, a positive value with low values indicates good glycemic control. Total risk of 1 or below is a good outcome. Scores of 2 or higher indicate larger or persistent excursions outside the range. CGM risk in these examples is based on 95 to 195 mg/dL target range so a score of 1 would occur if the subject was always at either of these limits. This analysis could be based on other target ranges or risk functions (e.g., 70 to 180 mg/dL) but these targets are consistent with medical concern observed in clinical studies. Any thresholds could be selected for this target zone. The CGM risk metric is penalized for glucose excursions outside these limits (e.g., parabolic function) that pushes up the score, particularly on the hypoglycemic side.

With respect to total risk with optimal bolusing at historic times, replay bolusing identifies the optimal amount of insulin at the same bolus time as the recorded data (e.g., pump or pen bolus time). Optimal bolus amounts reduces CGM risk by amount half. The decrease from 0.99 to 0.46 indicates there is an opportunity for improvements with therapy changes/bolus calculator changes. If replay analysis indicates that total risk can be significantly reduced (e.g., 25%, 50%, etc.) with an optimal strategy, then the subject or user can be prompted with therapy suggestions (e.g., visualization or message) that changes in insulin dosing may result in reduced exposure to glycemic risk. The scope is not limited to displaying results in this manner as there are many ways these potential risk reductions could be integrated into subsequent reports, analyses, and calculations.

With respect to total risk with optimal bolusing at estimated meal times, total risk can be further reduced and improved by adjusting the bolus timing. In this example, the decreased risk for this subject is from 0.46 to 0.39 compared to replay above of optimal amounts. This incremental risk reduction from the timing change is not as large as the previous step so that may indicate the historic data has insulin boluses that are close to the meal times. In other words, this subject's risk is less of an issue of timing and more an issue of amounts. In some embodiments, the replay analysis (comparing historical to meal time bolusing) can identify subject behavior that could be improved by dosing earlier or later than historic values. This is a comparison between recorded insulin bolus time and estimated/reconciled meal time. In addition to pumps, connected pens record when a bolus was delivered but there are sometimes questions about priming and if there occasional/additional doses from other pens or syringes.

Regarding IOB trace similarity score against optimal boluses at historical bolus times, an IOB trace is computed based on a record of actual boluses and an IOB trace of optimal treatments is computed. These traces can be compared as an inner product between unit magnitude traces to give a value ranging 0 to 1, where 1 indicates actual and optimal dosing is most similar in shape. A value of 1 indicates the same pattern in the trace even if they are different in overall magnitude. The value of 0.69, in this example, indicates that optimal bolus amounts at historical bolus times is a different IOB profile shape than current results. This similarity score can be thresholded or compared to current behavior and the output of this comparison can change smart alert behavior, user recommendations, report features, and visualizations. Depending on the implementation, the information can be conveyed as a qualitative score, a visualization or interpretation (e.g., "poor", "good", "great", etc.) of amounts and timing, for example. At a high level, the amount or timing of insulin dosing serves to compare current behavior and optimal behavior and these can be converted into a recommendation or visualization (e.g., score ranking or prioritization of need or benefit). The trace similarity looks at how close a subject is to ideal insulin levels and the result can also be interpreted to make a recommendation (replay reporting and/or real-time).

Scores can be compared to thresholds to determine if there is a risk. When there is a risk, an alert or other indicator may be generated and output, such as provided to the subject or a doctor for example. As the scores increase, the risk of glycemic dysfunction increases.

A comparison of the historical score with the estimated scores (and similarly the comparison of the risks) shows how much improvement (risk reduction) can be made by optimal or at least better bolusing.

The area 410 shows the subject's historical hyperglycemia risk profile (above the x-axis) and hypoglycemia risk profile (below the x-axis), identifying times of the day where the subject has consistently experienced glycemic dysfunction. The peak in the hyperglycemia risk profile identified as 410 indicates that the subject consistently experiences above-range BG between hours 1500-1600.

The area 420 shows the hyperglycemia and hyperglycemia risk profiles computed from a replay of the subject's data in which historical insulin bolus amounts are replaced by numerically optimal bolus amounts. The fact that the peak in historical hyperglycemia risk profile at 1500-1600 (in the area 410) is no longer present in the area 420 is an indication that the subject can substantially reduce exposure to hyperglycemia in the afternoon by injecting/infusing different amount of insulin without taking the additional step of choosing different bolus times. Similarly, reductions in hyperglycemia risk are possible by (i) injecting/infusing different amounts of prior to hour 2200 (by bolusing more accurately at the dinner meal) and (ii) injecting/infusing different amounts between 2300 and 0200 (by bolusing snacks prior to bed).

The area 430 shows the hyperglycemia and hyperglycemia risk profiles computed from a replay of the patient's data in which historical insulin bolus amounts are replaced by numerically optimal bolus amounts at times of estimated meals. The fact that there is a further reduction of hyperglycemic risk in the 1500-1600 timeframe (relative to the area 420) is an indication that the subject can reduce exposure to hyperglycemia in the afternoon by injecting/infusing insulin at times closer to meals, though based on this data for this subject the improvement is marginal. A more substantial improvement to hyperglycemia risk can be achieved between hours 2300 and 0600 by bolusing optimally and more consistently near meals/snacks in that timeframe.

Figure 5:
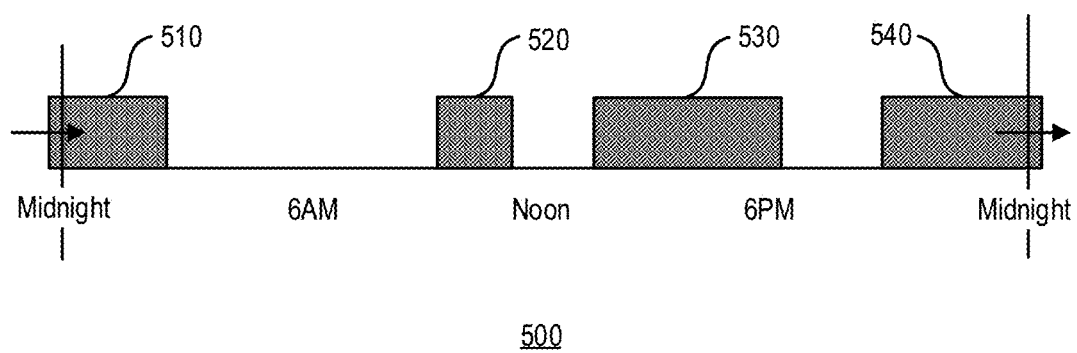
FIG. 5 is an illustration of risk zones according to an example.

FIG. 5 is an illustration 500 of risk zones 510, 520, 530, 540 according to an example. As shown, the risk profile plots 400 may be converted into zones of the day, which in this example indicates that there is under-dosing at lunch and at dinner. Risk zones 510, 520, 530, 540 show intervals of significant historical hyperglycemia risk that can be completely eliminated by bolusing at different times or in different amounts. The illustration may show the time of day effect across multiple days. In an implementation, the illustration 500 may be generated based on the results of the BG risk profile comparison function 334, by the BG risk comparator 240, and outputted by the output device 250. The historical hyperglycemic (above the x-axis) and hypoglycemic (below the x-axis) zones may be identified through the application of a threshold applied to the historical BG risk profiles produced by the profiling function of 322.

Figure 6:
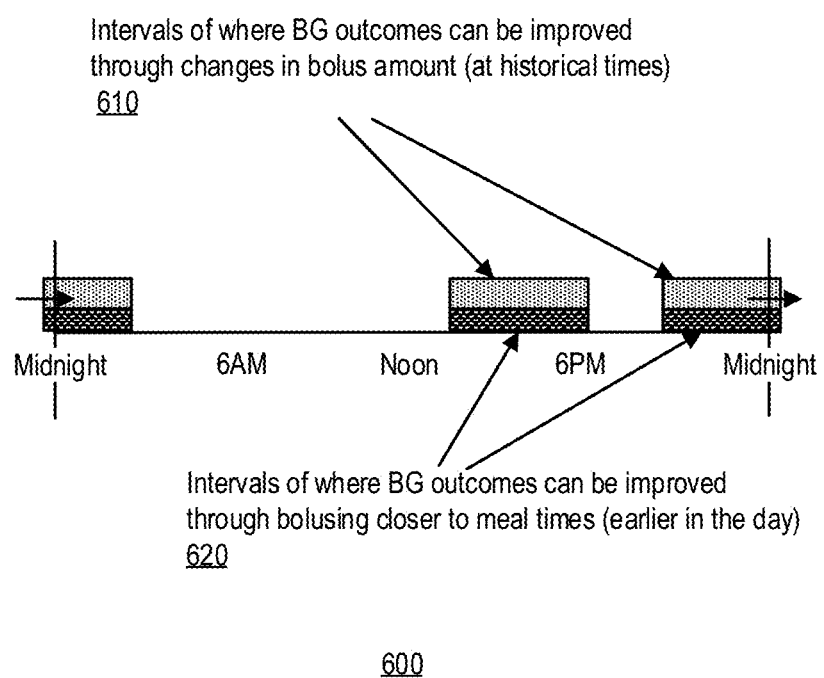
FIG. 6 is an illustration of zones of potential significant improvement from changing bolus doses or bolus timing according to an example.

FIG. 6 is an illustration 600 of zones of potential significant improvement (e.g., with respect to the risk profile plots 400) from changing bolus doses or bolus timing according to an example. The intervals 610 show intervals where BG outcomes can be improved through changes in bolus amount (at historical times). The intervals 620 show intervals where BG outcomes can be improved through bolusing closer to meal times (e.g., earlier in the day). Similar to generation and output of the illustration 500, in an implementation, the illustration 600 may be generated based on the results of the BG risk profile comparison function 334, by the BG risk comparator 240, and outputted by the output device 250. The historical hyperglycemic (above the x-axis) and hypoglycemic (below the x-axis) zones, respectively for numerically optimal bolusing at historical bolus times and for numerically optimal bolusing at validated estimated meal times, may be identified through the application of a threshold applied to the historical BG risk profiles produced by the profiling functions of 326 and 330.

Figure 7B:
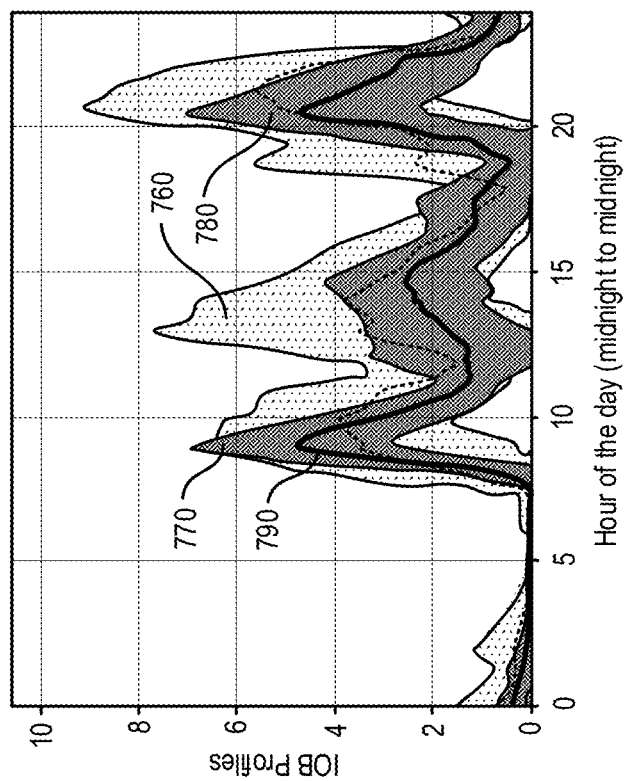
FIGS. 7A and 7B are illustrations of various insulin on board (IOB) profile plots according to an example.
Figure 7A:
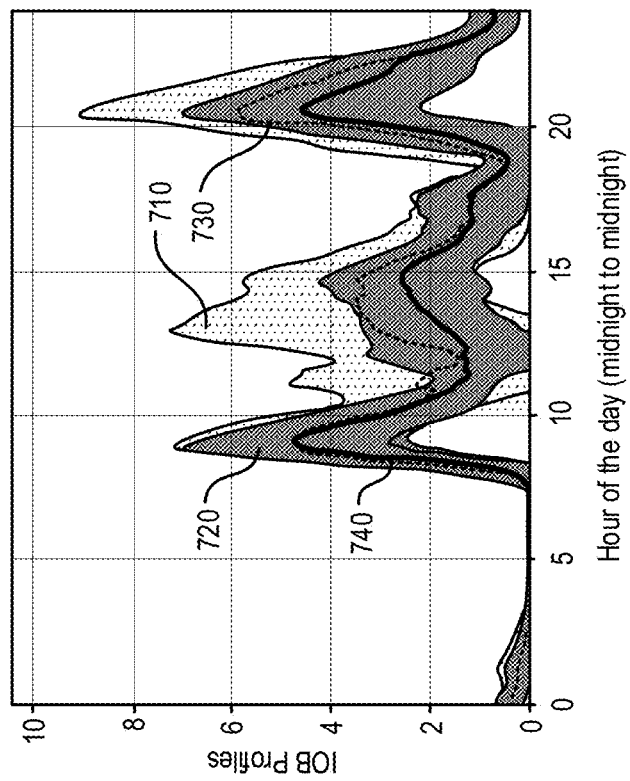

FIGS. 7A and 7B are illustrations of various insulin on board (IOB) profile plots 700, 750 according to an example. FIG. 7A shows (i) mean IOB for historical bolusing (line 740)+/−one standard deviation (area 720) and (ii) mean IOB for numerically optimal bolusing at historical bolus times (line 730)+/−one standard deviation (area 710). Although means and standard deviations are used in the examples herein, other statistics may be used depending on the implementation, such as medians, confidence intervals, standard errors, coefficients of variation, etc.

Similarly, FIG. 7B shows (i) mean IOB for historical bolusing (line 790)+/−one standard deviation (area 770) and (ii) mean IOB for numerically optimal bolusing at estimated meal times (line 780)+/−one standard deviation (area 760).

Note that in both FIGS. 7A and 7B, differences between lines 730, 780 and lines 740, 790 correspond to different amounts of insulin infused/injected in the recent past. For example, the gap between the lines 730 and 740 between hours 1200 and 1600 in FIG. 7A corresponds to the fact that with numerically optimal bolusing (at historical bolus times) more insulin is delivered (and "on board") compared to the historical boluses administered by the patient. Similar gaps can be seen between the lines 780 and 790 in FIG. 7B, even at times of the day where there is historically zero or very low IOB, corresponding to the difference between optimal bolusing at estimated meal times and optimal bolusing at historic bolus times.

The area 710 shows the variability in IOB (+/−one standard deviation) about the mean (line 730) associated with numerically optimal bolusing at historical bolus times.

The area 720 shows the variability in IOB (+/−one standard deviation) about the mean (line 740) associated with numerically optimal bolusing at estimated meal times.

The line 730 shows the mean IOB associated with numerically optimal bolusing at historical bolus times. The line 740 shows the mean IOB associated with numerically optimal bolusing at estimated meal times.

Figure 8:
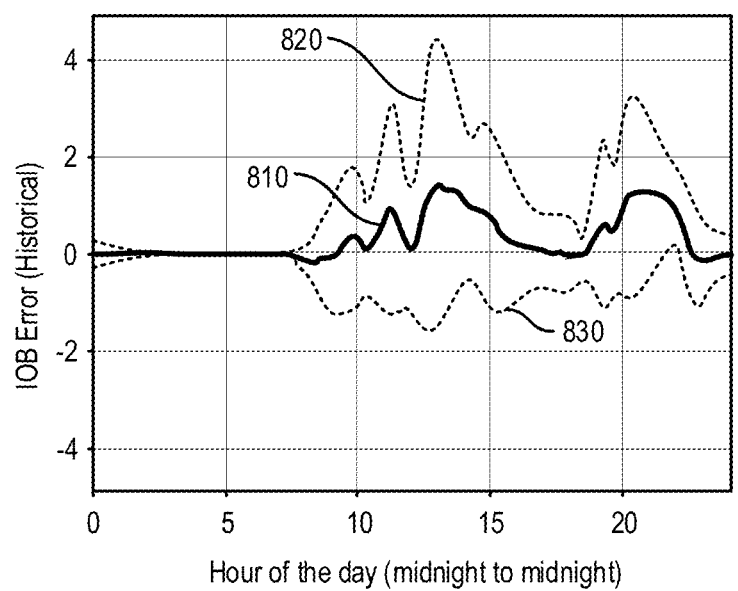
FIG. 8 is an illustration of an IOB discrepancy plot for bolusing at historical times according to an example.

FIG. 8 is an illustration of an JOB discrepancy plot 800, showing the mean difference between (i) IOB associated with numerically optimal bolusing at historical bolus times and (ii) IOB associated with historical boluses. The line 810 corresponds to the mean value of the JOB difference, and the 820 and 830 correspond to +/−one standard deviation, respectively. Times of the day where the mean value is positive correspond to times where numerically optimal bolusing results in higher IOB (on average) compared to historical bolusing. Smaller standard deviation values correspond to more consistent discrepancies between JOB associated numerically optimal bolusing and historical boluses. A positive value in the plot 800 indicates that there is typically more insulin with optimal dosing than historic dosing. Thus, an error profile for bolusing at historical times is provided.

The line 810 shows the mean difference between JOB associated with numerically optimal bolusing at historical bolus times and the historical boluses themselves.

The line 820 shows the mean difference above plus one standard deviation, providing a visual indication of the degrees of uncertainty about the difference between the means. It is noted that in some implementations, confidence interval may be used.

The line 830 shows the mean difference above minus one standard deviation, providing a visual indication of the degrees of uncertainty about the difference between the means. It is noted that in some implementations, confidence interval may be used.

Figure 9:
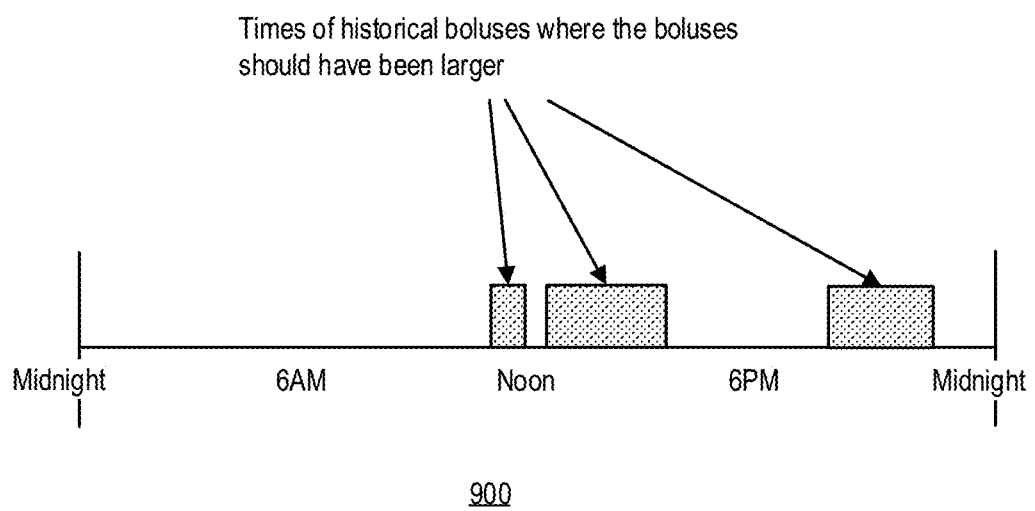
FIG. 9 is an illustration of an IOB discrepancy zones plot according to an example.

FIG. 9 is an illustration of an IOB discrepancy zones plot 900 for showing times of day where IOB associated with numerically optimal bolusing is substantially higher than IOB associated with historical boluses. The bars above the x-axis correspond to times of the day where the subject should consider taking larger boluses at historic bolus times. While none are shown for this example, bars below the x-axis correspond to times of the day where the subject should consider taking smaller boluses at historic bolus times.

Figure 10:
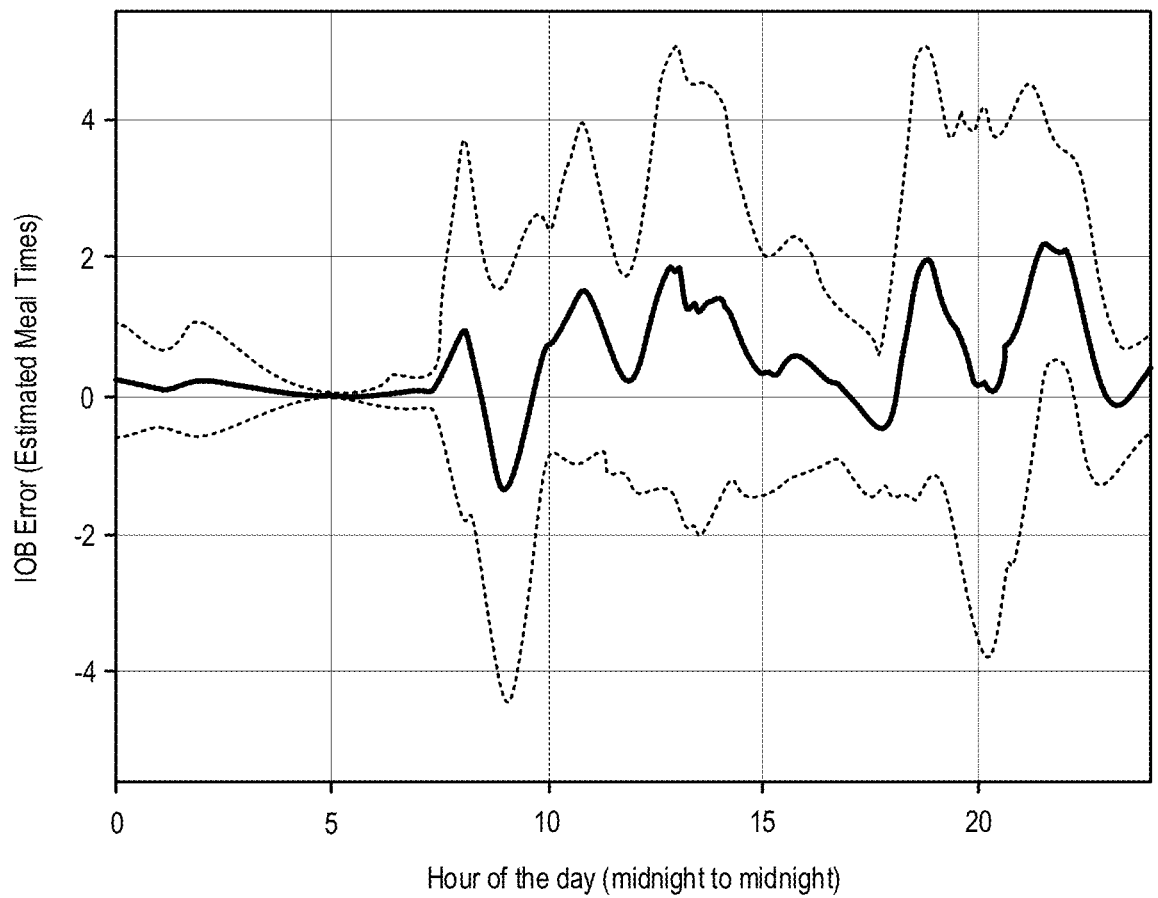
FIG. 10 is an illustration of an IOB discrepancy plot for optimal bolusing at estimated meal times according to an example.

FIG. 10 is an illustration of an IOB discrepancy plot 1000 for optimal bolusing at estimated meal times according to an example. Similar to FIG. 8, this plot shows the mean value of the difference between IOB associated with numerically optimal boluses and historic boluses, along with the +/−standard deviation envelope, though here for the difference between numerically optimal boluses at estimated meal times and historical boluses. Times of the day where the mean value is positive (negative) correspond to times where numerically optimal bolusing at estimated meal times would result in more (less, respectively) insulin on board on average than with historical bolusing. Here, the negative discrepancy that occurs at hour 0900 corresponds to the fact that the subject is bolusing at times different from estimated meals. Thus, an error profile relative to optimal bolusing at estimated meal times is provided.

Figure 11:
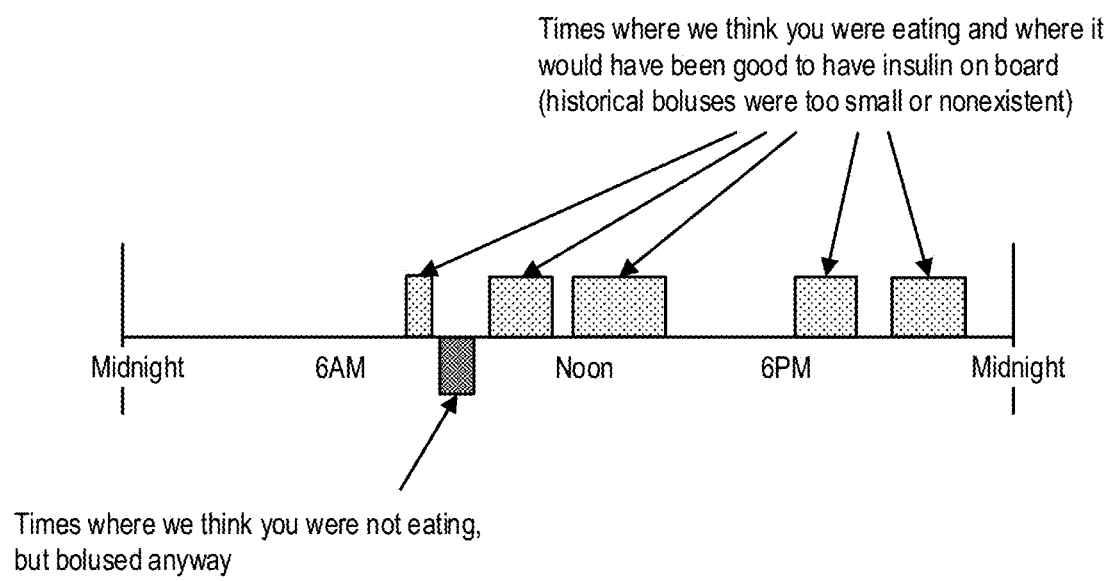
FIG. 11 is an illustration of an IOB discrepancy error zones plot relative to optimal bolusing at estimated meal times according to an example.

FIG. 11 is an illustration of an IOB discrepancy zones 1100 relative to optimal bolusing at estimated meal times according to an example. The zones above the x-axis are times where a subject may benefit from more insulin, either by giving a larger bolus than the historic amount or by giving a bolus that was not given historically. Here the zone below the x-axis at 0900 corresponds to time of the day where the subject should not be bolusing, preferring instead to bolus closer to actual meals times.

Figure 12:
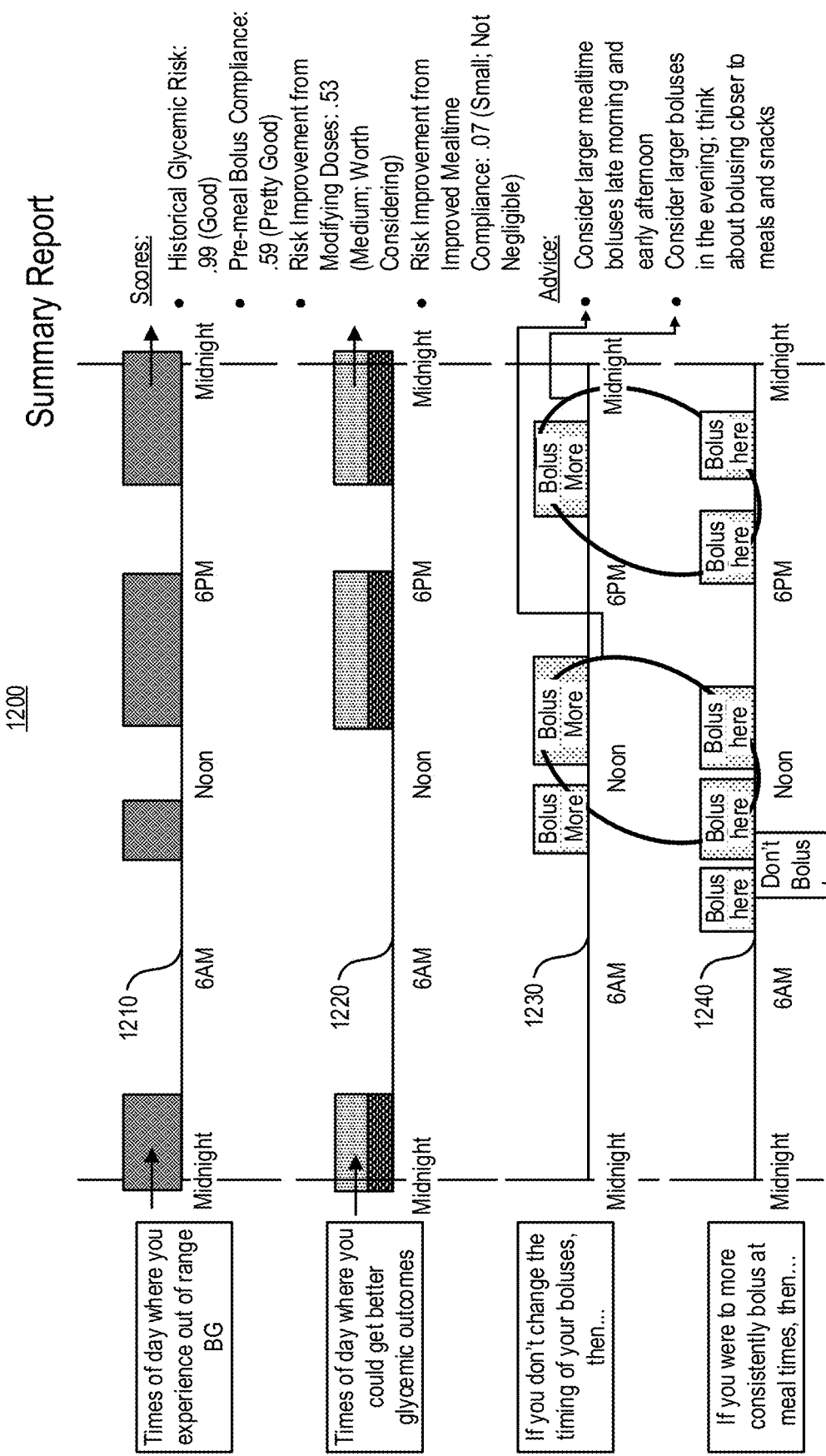
FIG. 12 is an illustration of an example summary report.

FIG. 12 is an illustration of an example summary report 1200, showing glycemic risk based on determined glycemic function. The summary report 1200 is just one example of a report that may be generated and provide for a subject or caregiver, and may be generated by stacking the plots and illustrations of FIGS. 5, 6, 9, and 11. The panel 1210 shows time segments of the profile with glycemic risk. The panel 1220 identifies time segments that would have had significantly lower risk in the replay with changes in the bolus strategy. The panel 1230 identifies time segments (e.g., meals) where the new bolus amounts (more insulin in this example) would act to significantly change the IOB. The panel 1240 identifies time segments (e.g., meals) where different bolus timing would act to significantly change the IOB. This can give a sense of priority on actions and treatment modifications, and identifies periods of the day where a larger bolus would reduce risk. On the panel 1240, non-optimal times to bolus may also be identified, and better alternatives may be suggested.

Figure 13:
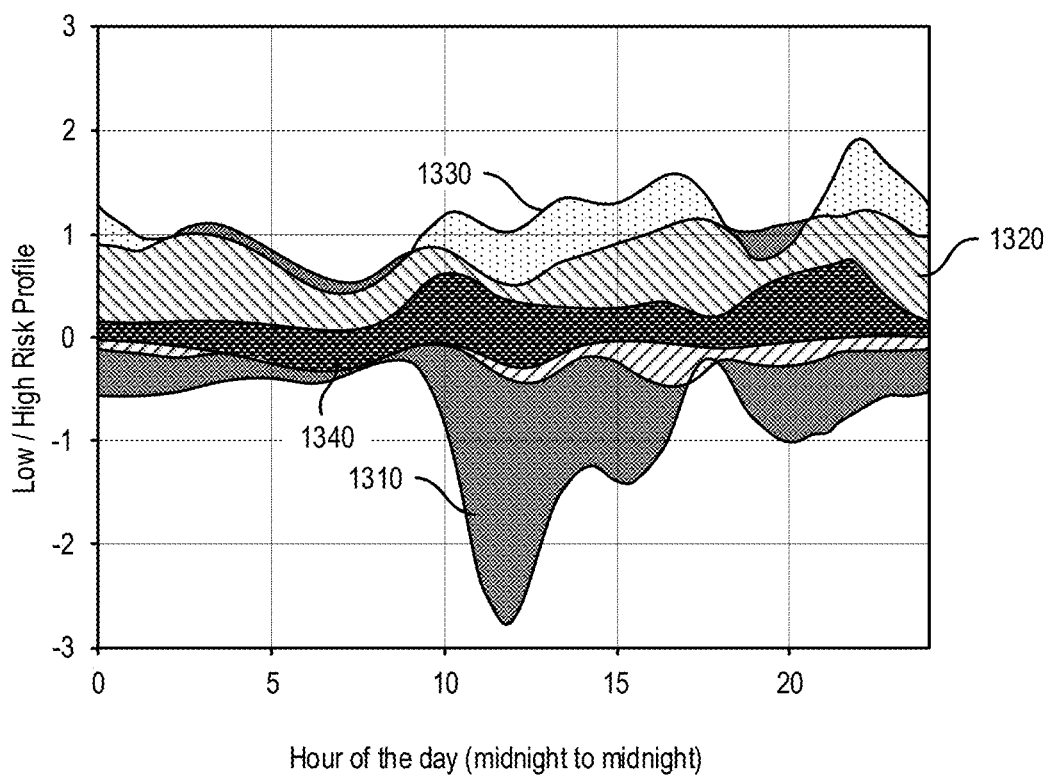
FIG. 13 is an illustration of various risk profile plots according to another example.

FIG. 13 is an illustration of various risk profile plots 1300 according to another example. In this example, for a subject, the total risk CGM is 1.75, the total risk with optimal bolusing at historical bolus times is 1.21, the total risk with optimal bolusing at estimated meal times is 0.55, the IOB trace similarity score against optimal boluses at historical bolus times is 0.60, and the IOB trace similarity score against optimal boluses at estimated meal times is 0.47. The number of days in the sample was 79 days.

The area 1310 shows a strong tendency to experience hypoglycemia at hour 1200 in the historical record, with the risk of hypoglycemia being significant more generally from hour 1000 to 1600, with moderate risk of hypoglycemia at hour 2000.

The area 1320 shows that the moderate risk of hypoglycemia at around hour 2000, can be addressed by bolusing differently at historical bolus times, though without changing the times of boluses, the reduction of hypoglycemia in the evening comes at the expense of a new substantial risk of hyperglycemia at around hour 2200.

The area 1330 shows that the strong risk of hypoglycemia at around hour 1200, can be addressed by bolusing differently at historical bolus times, though without changing the times of boluses, the reduction of hypoglycemia during the day comes at the expense of a new substantial risk of hyperglycemia from between hours 1000 and 1800.

The area 1340 shows that with numerically optimal bolusing at times of estimated meals the subject can effectively avoid exposure both hypoglycemia and hyperglycemia.

Figure 14A:
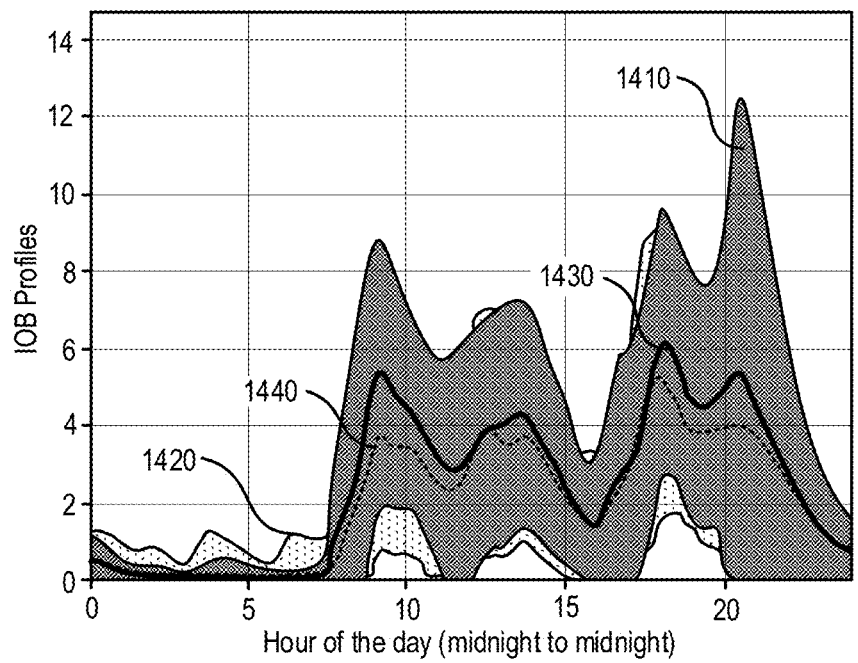
FIGS. 14A and 14B are illustrations of various IOB profile plots according to another example.
Figure 14B:
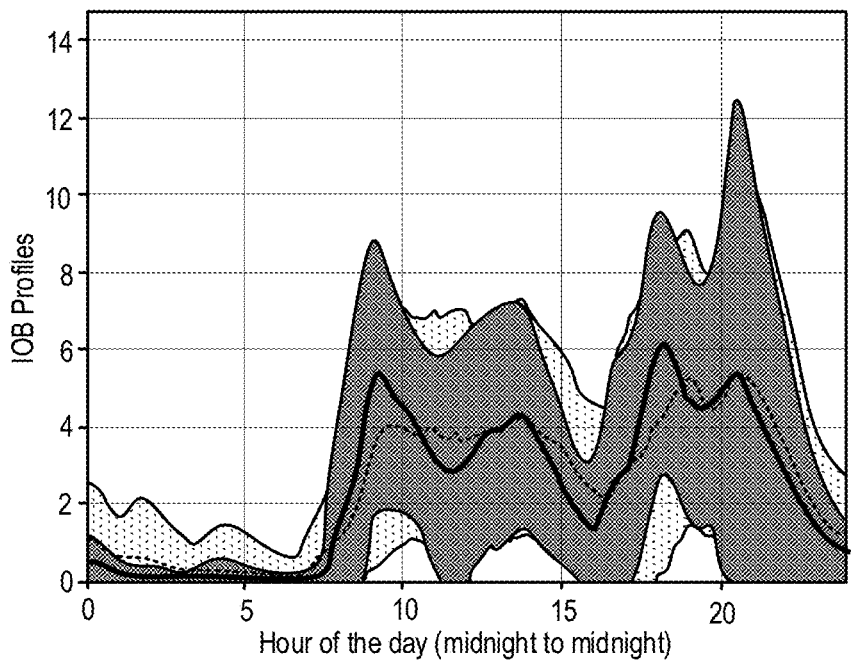

FIGS. 14A and 14B are illustrations of various IOB profile plots 1400, 1450, respectively, according to another example. The line 1410 shows a large value of mean IOB at hour 2100 (with large variability) resulting from historical bolusing, compared to a smaller mean (and less variable) IOB resulting from numerically optimal boluses at historical bolus times.

The line 1420 shows high variability about the mean IOB resulting from numerically optimal bolusing at historic bolus times at around hour 0730. Here the mean IOB due to numerically optimal bolusing is itself very small, because there are not many historical boluses at that time of day. Note that, in FIG. 14B, at the same time of day, mean IOB associated with boluses at estimated meal times is larger than mean IOB associated with historical boluses, indicating that the subject may be consistently delaying boluses for the first meal of the day.

The line 1430 shows a large value of mean IOB at hour 1700 (with large variability) resulting from historical bolusing, compared to a smaller mean (and less variable) IOB resulting from numerically optimal boluses at historical bolus times.

The line 1440 shows that IOB at 0830 due to numerically optimal bolusing is lower than the mean IOB associated with the historical bolus record. This is true as well in FIG. 14B at the same time of day. Thus, regardless of the timing of boluses in the morning, the subject is taking too much insulin, and this is related to the strong tendency to experience hypoglycemia in the morning.

Figure 15A:
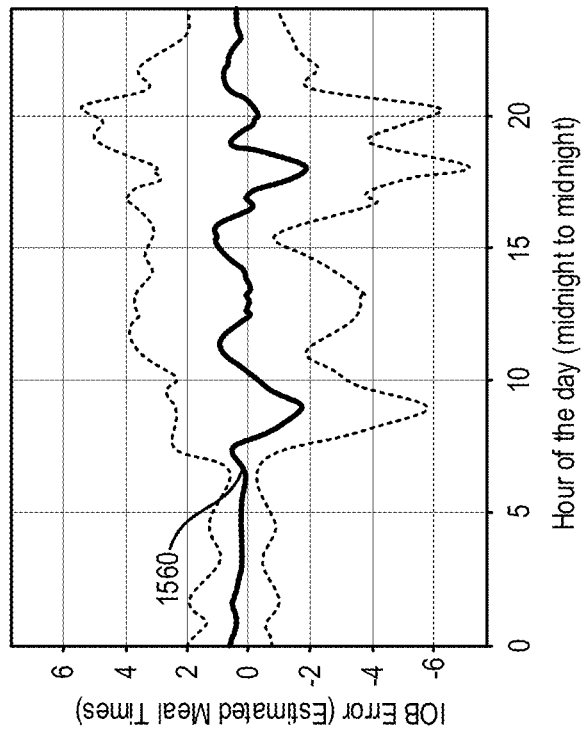
FIGS. 15A and 15B are illustrations of various IOB discrepancy plots according to another example.
Figure 15B:
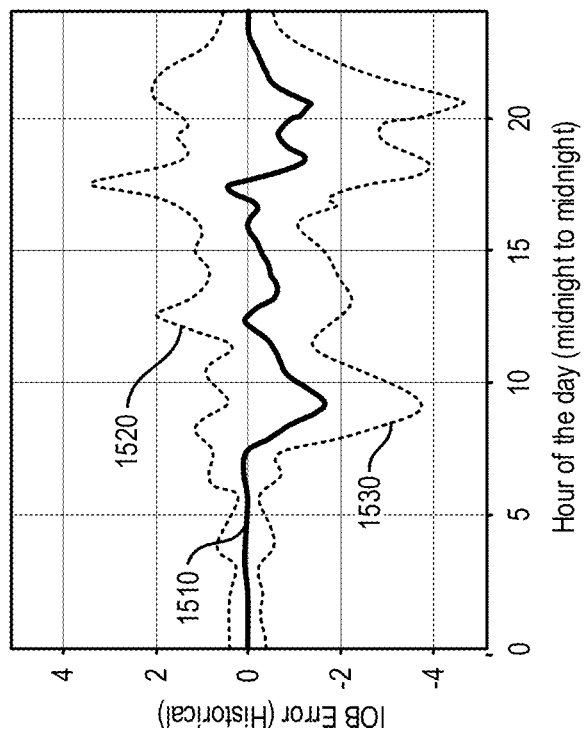

FIGS. 15A and 15B are illustrations of various IOB discrepancy plots 1500, 1550, respectively, according to another example. The fact that the discrepancy (as indicated by the solid line 1510) is negative throughout the day (e.g., from about 0730 to about 2300) in FIG. 15A indicates that, when constrained to bolusing at historical bolus times, the subject should be bolusing less. The fact that the mean discrepancy (as indicated by the solid line 1560) in FIG. 15B oscillates between positive and negative values indicates that the subject would have (and would benefit from) substantially different IOB throughout the day.

The solid line 1510 shows the mean difference between IOB associated with numerically optimal bolusing at historical bolus times and the historical boluses themselves.

The dashed line 1520 shows the mean difference above plus one standard deviation, providing a visual indication of the degrees of uncertainty about the difference between the means.

The dashed line 1530 shows the mean difference above plus one standard deviation, providing a visual indication of the degrees of uncertainty about the difference between the means.

Figure 16:
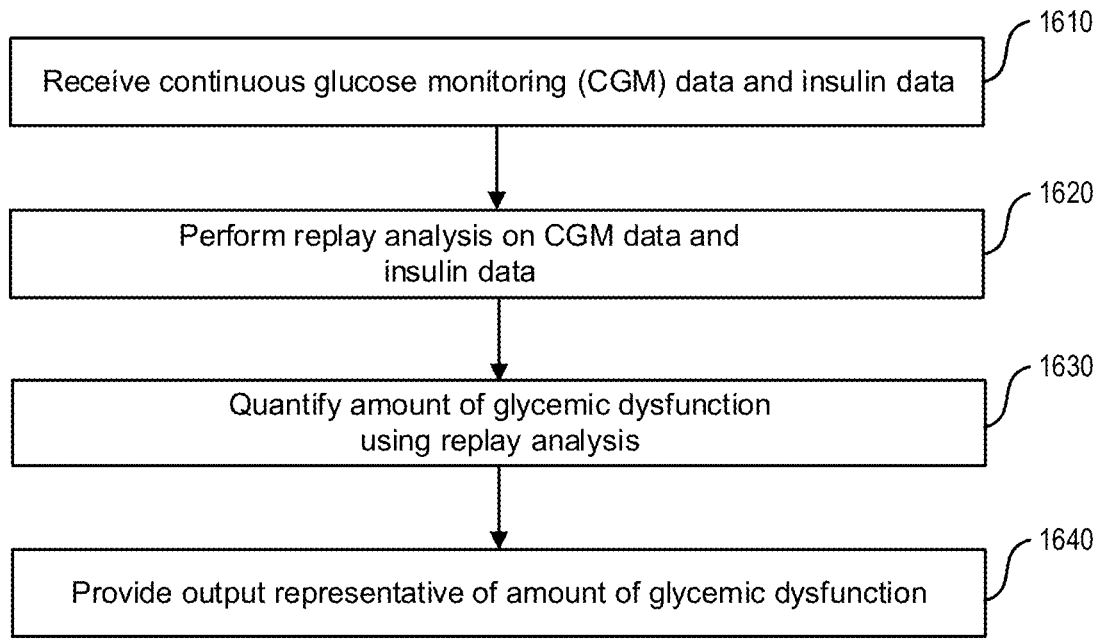
FIG. 16 is an operational flow of an implementation of a method for determining an amount of glycemic dysfunction.

FIG. 16 is an operational flow of an implementation of a method 1600 for determining an amount of glycemic dysfunction. At 1610, CGM data and insulin data pertaining to a subject (such as the subject 140) is received, e.g., at a replay analyzer such as the replay analyzer 220. The CGM data and insulin data may comprise subject provided data 207, the data 210, and/or the functions 215. The CGM data and insulin data may be received from a storage device, such as a database comprising CGM records and insulin records of the subject 140. Alternatively or additionally, the data may be received from the subject 140 (e.g., via the subject computing device 205), from CGM and/or insulin devices or monitors (e.g., the insulin device 110, the glucose monitor 120, the activity monitor 150, and/or the smartphone 160), or other equipment or entities. In implementations that are used for replay analysis, historical data may be used. It is useful to have an accurate estimation of both timing and amount of meals in the historical data.

At 1620, a replay analysis is performed on the CGM data and insulin data, e.g., by the replay analyzer 220. The steps of this analysis include (i) the use of a meal estimation function (such as the meal compiler 303) that produces an estimate of meal events (particularly carbohydrate intake) (such as the estimated meals data 306) in the historical record based on the analysis of trends and patterns in the CGM data and insulin data time series data and (ii) the use of a replay predictive function 305 (such as the output of the replay compiler 304) that uses the estimated meal time series to simulate the historical data starting from any point in the historical time series from any particular metabolic initial condition and allows the specification of either historical or optimized insulin boluses.

At 1630, an amount of glycemic dysfunction is quantified based on the replay analysis, e.g., using one or more of the IOB assessor 225, the BG risk profiler 230, the IOB profiler 235, the BG risk comparator, and the discrepancy analyzer 245, as described further herein. The analysis may include (i) computing hyperglycemic and hypoglycemic risk profiles (such as the profiling performed at 322) based on the totality of historical CGM data, where the profile value at any point in a 24-hour day long period describes the clinical significance of historical exposure to hyperglycemia (respectively, hypoglycemia) at that time of the day, normalized to so that the specification of a hyperglycemic (respectively, hypoglycemic) risk threshold marks intervals of significant glycemic risk during the day, (ii) using the replay predictive function to simulate (replay) the entire record replacing historical boluses with boluses that are numerically optimal based on predicted responses from the replay function (such as described with respect to element 312), (iii) using the replay predictive function to simulate (replay) the entire record canceling historical boluses and inserting numerically optimal boluses at times of estimated meals (such as described with respect to element 314), (iv) computing hyperglycemic and hypoglycemic risk profiles for the replayed time series using numerically optimal boluses at times of historical boluses (such as described with respect to element 326), and (v) computing hyperglycemic and hypoglycemic risk profiles for the replayed time series using numerically optimal boluses at times of estimated meals (such as described with respect to element 330).

The BG risk profiler 230 includes a calculation to convert one or more blood glucose values into a relative risk score consistent with the risk of diabetic complications or degree of glycemic control. The risk scores can be assigned to a single value or summarized over a time segment such as a daily average risk score. In one example, the metric is a positive value with low values indicating good glycemic control, such as staying within a target zone or close to a target value. If the target blood glucose range was 95 to 195 mg/dL then an example risk function would map a reading at 95 mg/dL to a risk of 1.0, a reading at 120 mg/dL to a risk of 0.2 and a reading at 195 mg/dL to a risk of 1.0. As a result, a subject that stayed inside the target range would have a total risk less than 1 and a subject with tight control would have a risk closer to zero.

Continuing this example, blood glucose values in hyperglycemia and hypoglycemia regions are given increasingly higher risk scores as the glucose moves away from the target values. The risk function would map a reading at 65 mg/dL to a risk of 2.5 and a reading at 225 mg/dL to a risk of 2.0. Thus, scores of 2 or higher indicate larger or persistent excursions outside the target range. The penalty function is not symmetric in this case as it puts a larger penalty on hypoglycemic values. The shape of the risk function can be based on a mathematical function, such as a quadratic or lognormal curve or set of linear functions. One known metric is average daily risk range (see e.g., Kovatchev B. P. et al., "Evaluation of a New Measure of Blood Glucose Variability in Diabetes", Diabetes Care, 2006 November; 29(11):2433-8, https://www.ncbi.nlm.nih.gov/pubmed/17065680. In other cases, it can be empirically derived from a subject's historical data or further adjusted for the treatment goals.

The risk function can include and emphasize other factors related to diabetic risk. One example is a risk metric called (see e.g., U.S. Pat. No. 9,439,602 entitled "Alert System for Hypo and Hyperglycemia Prevention Based on Clinical Risk") that explicitly considers the rate of change of glucose as a threat factor for the patient (e.g., risk levels in hypoglycemia and hyperglycemia are amplified in the presence of a decreasing and increasing glucose trend, respectively).

The three sets of risk profiles are evaluated in a BG risk profiles comparison function (such as the BG risk profile comparison function 334), that computes total blood glucose scores respectively for the historical data, for replayed data with numerically optimal boluses at historical bolus times, and for replayed data with numerically optimal boluses at times of estimated meals. Differences between these respective scores are indicative of dysfunction associated with suboptimal boluses at times of historical boluses and/or boluses not occurring at times of the estimated meals (corresponding to a replay bolus timing effect).

In addition, to compute a measure of pre-meal bolus compliance, time series of IOB are computed for (i) the historical time series of insulin delivery (such as described with respect to element 316), (ii) the replayed time series of numerically optimal boluses at times of historical boluses (such as described with respect to element 318), and (iii) the replayed time series of numerically optimal boluses at times of estimated meals (such as described with respect to element 320). From these IOB time series, 24-hour profiles of IOB can be computed, where the value of the profile at any time corresponds to a first order statistic on the amount of insulin (e.g., average insulin) that the patient has on board at time of the day, either historically, or with numerically optimal boluses at historical bolus times, or with numerically optimal boluses at times of estimated meals. These respective IOB profiles allow the assessment of IOB discrepancy between (i) historical bolusing and numerically optimal boluses at historical bolus times (such as described with respect to element 336) and (ii) historical bolusing and numerically optimal bolusing at time so of estimated meals (such as described with respect to element 340). In addition, the three sets of IOB time series admit the computation of a numerical similarity measure between (i) historical bolusing and numerically optimal boluses at historical bolus times (such as described with respect to element 338) and (ii) historical bolusing and numerically optimal bolusing at time of estimated meals (such as described with respect to element 342).

At 1640, an output representative of the amount of glycemic dysfunction is provided via an output device such as the output device 250, e.g., to computing device associated with a subject, a physician, or another entity. The output may comprise plots or other information and recommendations such as those described further herein (e.g., a summary report such as the report 1200 of FIG. 12). Such output may provide indicators of replay bolus timing effects and pre-meal bolus compliance. One or more implementations quantify the effects of misinformation about meals (both in terms of timing and composition). Accordingly, the benefits (e.g., risk reduction) of insulin is evaluated with respect to an optimal dose and with respect to changing optimal pre-meal timing.

Figure 17:
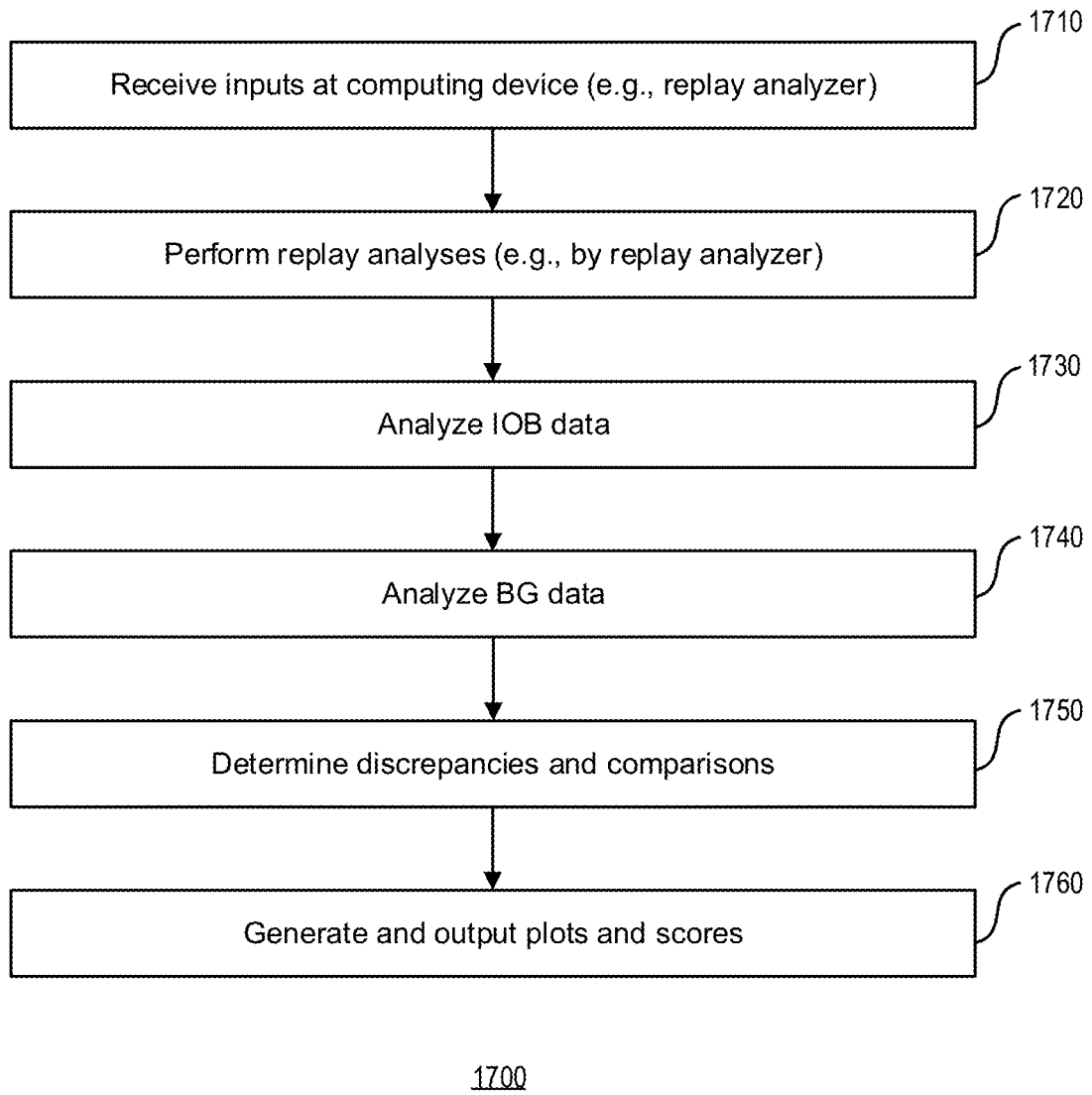
FIG. 17 is an operational flow of another implementation of a method for determining an amount of glycemic dysfunction.

FIG. 17 is an operational flow of another implementation of a method 1700 for determining an amount of glycemic dysfunction. At 1710, inputs are received at a computing device, such as the computing device 201. In an implementation, the inputs may comprise the subject provided data 207, the data 210, and/or the functions 215, and may be received at the replay analyzer 220. The inputs may comprise CGM data and insulin data, similar to that described with respect to 1610 (e.g., historical BG 301 and historical insulin 302).

At 1720, replay analyses are performed (e.g., by the replay analyzer 220) for historical boluses and for estimated meals, using aspects described with respect to 312 and 314 for example. In this manner, it may be determined what would have happened if the subject bolused at times of historical boluses, and what would have happened if the subject bolused at times of estimated meals.

At 1730, IOB data analysis is performed, such as that described with respect to FIGS. 3A and 3B. In an implementation, the IOB data analysis may be performed by the IOB assessor 225 and/or the IOB profiler 235. At 1740, BG data analysis is performed, such as that described with respect to FIGS. 3A and 3B. In an implementation, the BG data analysis may be performed by the BG risk profiler 230 and/or the BG risk comparator 240. Such analyses may include various assessments and profilings as described further above.

At 1750, discrepancies are determined along with comparisons, as detailed above with respect to FIGS. 3A and 3B. In an implementation, the discrepancies may be determined by the discrepancy analyzer 245. At 1760, plots and scores, such as those described further herein, may be generated and outputted, e.g., via the output device 250.

Figure 18:
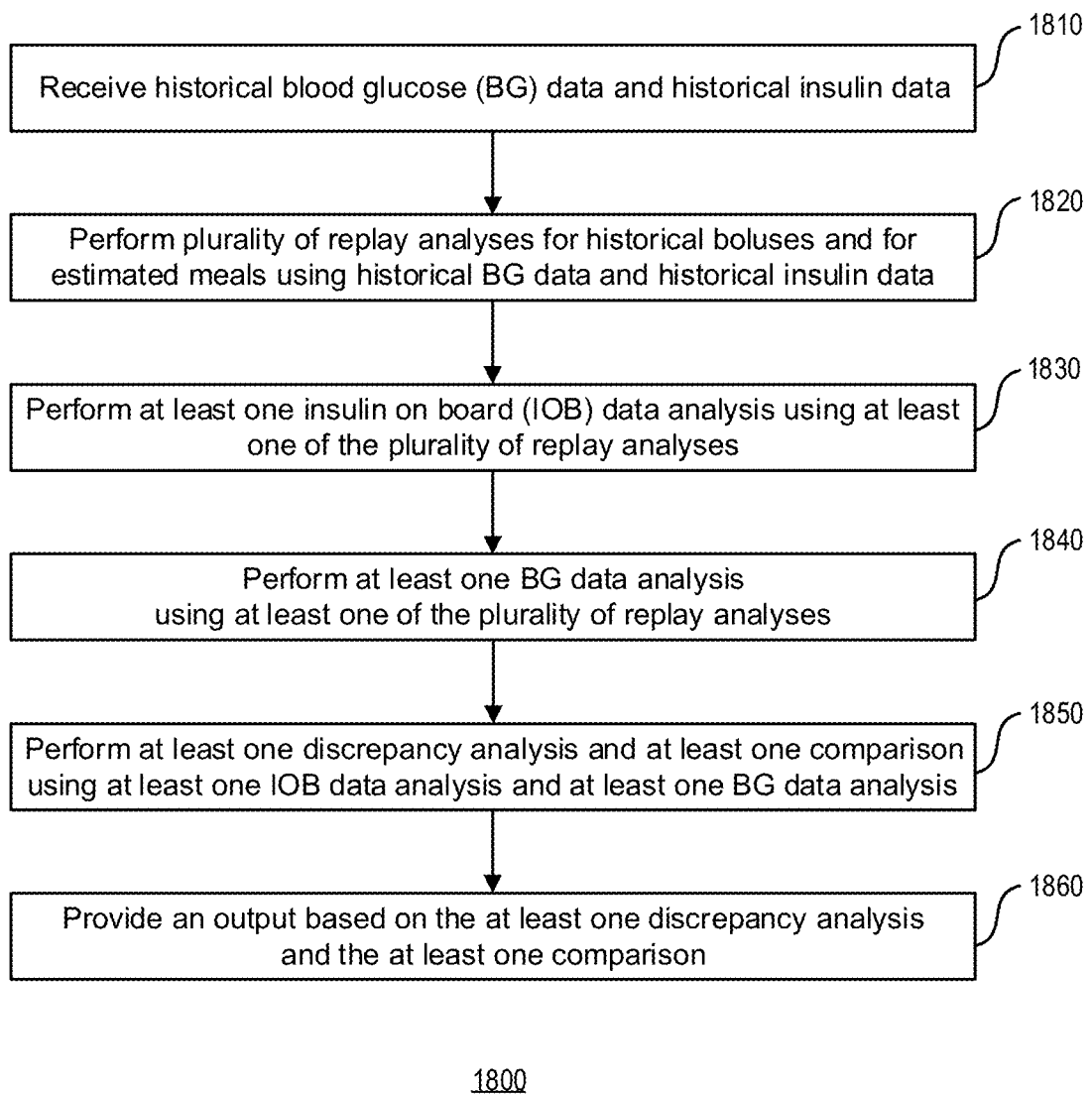
FIG. 18 is an operational flow of another implementation of a method for determining an amount of glycemic dysfunction.

FIG. 18 is an operational flow of another implementation of a method 1800 for determining an amount of glycemic dysfunction. The method may be performed by the computing device 201 in some implementations.

At 1810, historical BG data and historical insulin data are received at a replay analyzer, such as the replay analyzer 220. A plurality of replay analyses are performed at 1820 by the replay analyzer 220 for historical boluses and for estimated meals using the historical BG data and the historical insulin data.

At 1830, at least one IOB data analysis is performed using at least one of the plurality of replay analyses. The IOB data analysis may be performed using one or more of the IOB assessor 225 or the IOB profiler 235, for example. At 1840, at least one BG data analysis is performed using at least one of the plurality of replay analyses. The BG data analysis may be performed using one or more of the BG risk profiler 230 or the BG risk comparator 240, for example.

At 1850, at least one discrepancy analysis is performed and at least one comparison is performed using the at least one IOB data analysis and the at least one BG data analysis. The discrepancy analysis and/or comparison may be performed by the discrepancy analyzer 245, for example.

At 1860, an output, such as those described further herein, is provided. The output may be provided by the output device 250, and may be based on the at least one discrepancy analysis and the at least one comparison.

Figure 19:
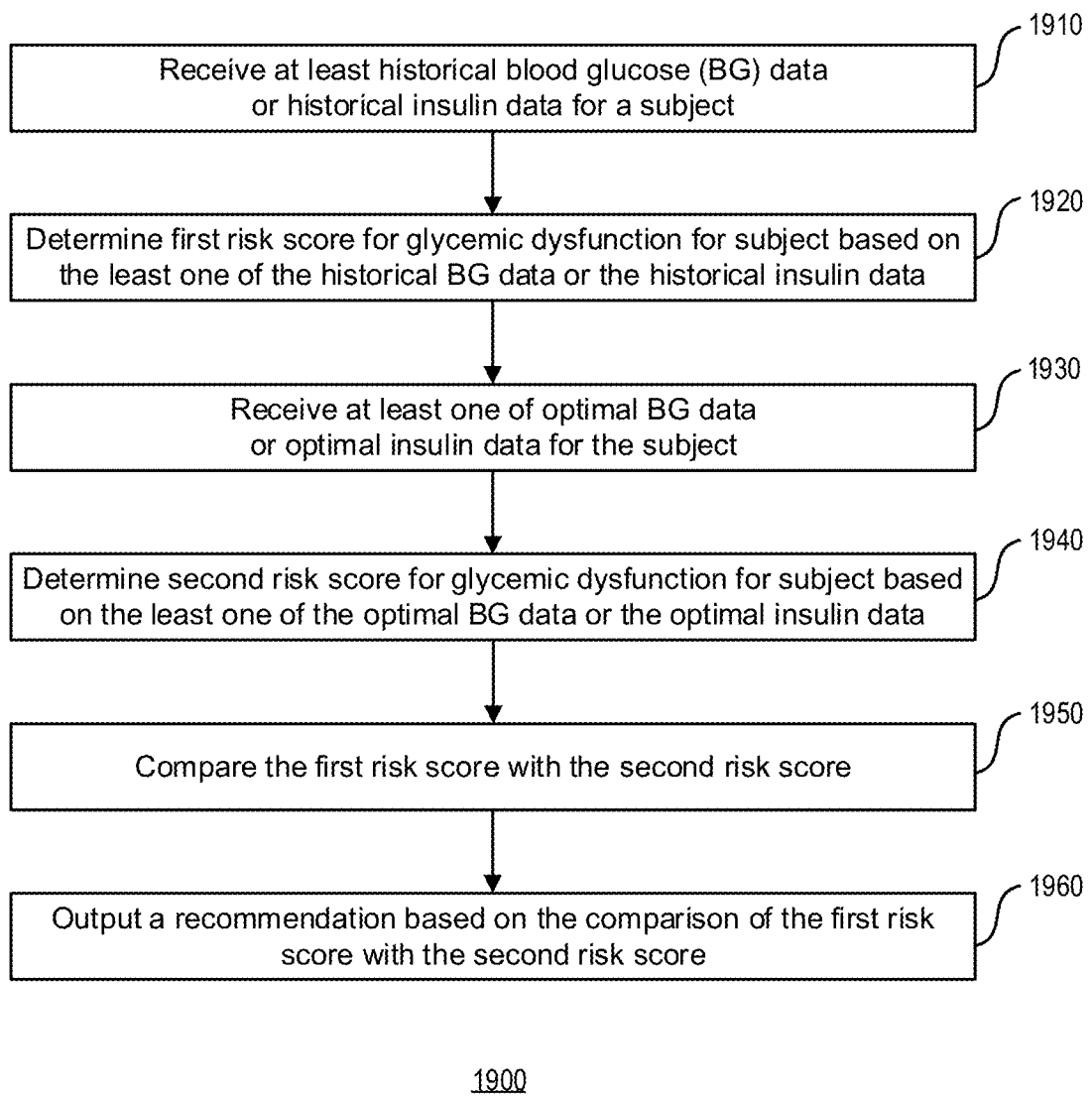
FIG. 19 is an operational flow of another implementation of a method for determining an amount of glycemic dysfunction.

FIG. 19 is an operational flow of another implementation of a method 1900 for determining an amount of glycemic dysfunction. The method may be performed by the computing device 201 in some implementations.

At 1910, at least one of historical BG data or historical insulin data for a subject is received at a replay analyzer, such as the replay analyzer 220. At 1920, a first risk score is determined for glycemic dysfunction for the subject based on the at least one of the historical BG data or the historical insulin data. The risk score may be determined by the replay analyzer 220, for example. In one example, the risk score can be a value from the BG risk profiler 230. In another example, the output from the BG risk profiler 230 is converted into a risk score with a set of thresholds or zones, such as risk below 1 is assigned a low risk score, risk from 1 to 2 is assigned as moderate risks, and risk greater than 2 is assigned as high risk. These thresholds and zones can be preset or customized for each patient based on historical values or current goals. A risk score can also be used to summarize the BG risk profile associated with different time of the day, meals, and/or other relevant events.

At 1930, at least one of optimal BG data or optimal insulin data for the subject is received at a replay analyzer, such as the replay analyzer 220. At 1940, a second risk score is determined for glycemic dysfunction for the subject based on the at least one of the optimal BG data or optimal insulin data. The risk score may be determined by the replay analyzer 220, for example. This risk score can use the same attributes as the risk score calculated in 1910 such that potential improvements can be evaluated. For example, the risk score for breakfast will be compared between the historical data and the optimal data.

At 1950, the first risk score is compared with the second risk score, by the replay analyzer 220 for example. A recommendation may be generated and output at 1960, e.g., by the replay analyzer 220 and/or the output device 250 in some implementations, based on the comparison at 1940. The recommendation may be optimal BG data or optimal insulin data for a subject or other user regarding instructions or other suggestions for improving or maintaining their glycemic information (e.g., to reduce glycemic dysfunction in some implementations as shown in FIG. 12). When the first risk score is close to the second risk score (e.g., less than a predetermined percentage difference, within a score range or difference, less than a threshold difference, etc.), the subject behavior is identified and encouraged as the amount of insulin and timing are close to ideal. When the first risk score is significantly larger than the second risk score (e.g., greater than or equal to a predetermined percentage difference, outside of a score range or difference, equal to or larger than a threshold difference, etc.), then there is an opportunity for treatment optimization by adjusting the amount or timing of the insulin bolus for similar meals in the future.

Output recommendations at 1960 can be generated in a variety of formats so as to best match the subject needs. In one embodiment, the recommendation can be qualitative, such as identifying that dosing earlier before breakfast would help avoid high glucose values in the following hour. For example, in some implementations, the recommendations can be prompts on a screen or they can be overlaid on a plot showing the glucose excursion. Alternatively or additionally, the recommendations can be a summary report that covers a period of time like a week or month. The summary report can identify periods of the day that have high glycemic risk and assign possible causes. For example, this report might identify that low glucose values in the afternoon result from dosing too much insulin for lunch combined with dosing after the meal was eaten.

Figure 20:
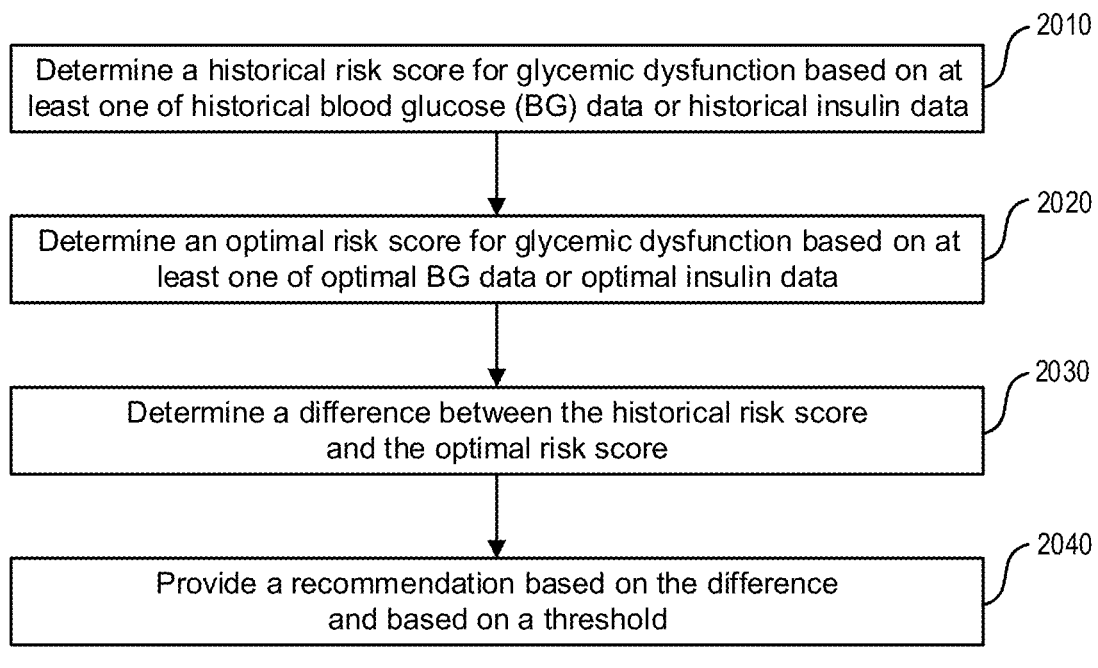
FIG. 20 is an operational flow of another implementation of a method for determining an amount of glycemic dysfunction.

FIG. 20 is an operational flow of another implementation of a method 2000 for determining an amount of glycemic dysfunction. The method may be performed by the computing device 201 in some implementations. Operation 2010 involves the determination of a historical risk score based on at least one of historical blood glucose data or historical insulin data, which in terms of an implementation of FIGS. 3A and 3B involves elements 322 (for the computation of the risk profile) and 334 (for the computation of the risk score). Operation 2020 involves computing an optimal risk score for glycemic dysfunction based on at least one optimal BG data or optimal insulin, which in terms of an implementation of FIGS. 3A and 3B involves elements 312 (for numerically optimal bolusing at historical bolus times) or 314 (for numerically optimal bolusing at estimated meal times), 326 or 330 (for optimal risk profiles, respectively), and 334 (for the computation of the risk scores, respectively). Operation 2030 involves determining the difference between the historical risk score and the optimal risk score, which in terms of an implementation of FIGS. 3A and 3B involves element 334. Operation 2040 provides a recommendation based on the difference and based on a threshold.

At 2010, a historical risk score for glycemic dysfunction is determined based on at least one of historical BG data or historical insulin data for a subject, which may have been received at the replay analyzer 220 for example.

At 2020, an optimal risk score for glycemic dysfunction is determined based on at least one of optimal BG data or optimal insulin data for a subject, which may have been received at the replay analyzer 220 for example.

At 2030, a difference between the historical risk score and the optimal risk score is determined, e.g., by the replay analyzer 220.

At 2040, a recommendation may be generated and output, e.g., by the replay analyzer 220 and/or the output device 250 in some implementations, based on the determined difference.

FIG. 21 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 21, an exemplary system for implementing aspects described herein includes a computing device, such as computing device 2100. In its most basic configuration, computing device 2100 typically includes at least one processing unit 2102 and memory 2104. Depending on the exact configuration and type of computing device, memory 2104 may be volatile (such as random access memory (RAM)), non-volatile (such as read-only memory (ROM), flash memory, etc.), or some combination of the two. This most basic configuration is illustrated in FIG. 21 by dashed line 2106.

Computing device 2100 may have additional features/functionality. For example, computing device 2100 may include additional storage (removable and/or non-removable) including, but not limited to, magnetic or optical disks or tape. Such additional storage is illustrated in FIG. 21 by removable storage 2108 and non-removable storage 2110.

Computing device 2100 typically includes a variety of computer readable media. Computer readable media can be any available media that can be accessed by the device 2100 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 2104, removable storage 2108, and non-removable storage 2110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2100. Any such computer storage media may be part of computing device 2100.

Computing device 2100 may contain communication connection(s) 2112 that allow the device to communicate with other devices. Computing device 2100 may also have input device(s) 2114 such as a keyboard, mouse, pen, voice input device, touch input device, etc. Output device(s) 2116 such as a display, speakers, printer, etc. may also be included. All these devices are well known in the art and need not be discussed at length here.

In an implementation, a method of determining an amount of glycemic dysfunction is provided. The method comprises receiving continuous glucose monitoring (CGM) and insulin data pertaining to a subject, wherein the CGM and insulin data comprise an insulin bolus amount and a timing for the insulin bolus amount, performing a replay analysis on the CGM and insulin data, quantifying an amount of glycemic dysfunction using the replay analysis, and providing an output representative of the amount of glycemic dysfunction.

Implementations may include some or all of the following features. A first portion of the CGM and insulin data is estimated and a second portion of the CGM and insulin data is reported. The CGM and insulin data comprise at least one of an estimated timing of a meal of the subject or an estimated composition of the meal of the subject. The CGM and insulin data comprise misinformation about at least one of a timing of a meal of the subject or a composition of the meal of the subject. A portion of the CGM and insulin data is received from the subject. The CGM and insulin data comprise estimated metabolic states in time series form, a reconciled meal history, and a delivered insulin history. The CGM and insulin data comprise estimated metabolic states, reconciled estimated metabolic inputs, and known metabolic inputs. The CGM and insulin data is discretized in time.

Implementations may also include some or all of the following features. Performing the replay analysis on the CGM and insulin data comprises isolating an impact of timing, carbohydrate counting, and carbohydrate ratio of an estimated bolusing with respect to a meal. Performing the replay analysis on the CGM and insulin data comprises using replay simulation analysis to assess an impact of numerically optimal boluses at historical bolus times by removing inaccurate carbohydrate counts and inappropriate carbohydrate ratios. Performing the replay analysis on the CGM and insulin data comprises assessing an impact of numerically optimal boluses at estimated historical meal times. Performing the replay analysis on the CGM and insulin data comprises performing replay simulations with at least one of historical CGM and insulin data, numerically optimal boluses at historical bolus times, or numerically optimal boluses at estimated meal times. Performing the replay analysis on the CGM and insulin data comprises generating a set of candidate boluses, simulating future blood glucose (BG) values associated with each candidate bolus, scoring a simulated BG trajectory for each candidate bolus using a risk analysis, picking and implementing the best bolus based on the score of each candidate bolus, and continuing to replay simulate until the time of the next bolus. The risk analysis is a velocity dependent risk analysis.

Implementations may also include some or all of the following features. Quantifying the amount of glycemic dysfunction comprises quantifying the amount of dysfunction of estimated bolusing compared to an optimally timed bolusing. Quantifying the amount of glycemic dysfunction comprises quantifying the amount of dysfunction of historical bolusing compared to an optimally timed bolusing. Quantifying the amount of glycemic dysfunction comprises quantifying a compliance of the patient with an ideal pre-meal bolus timing.

Implementations may also include some or all of the following features. The output comprises at least one of a plot or a visualization. The output comprises a risk index comprising at least one of high blood glucose risk, low blood glucose risk, or total glycemic risk. The output comprises a number and an extent of excursions into an out-of-range blood glucose level. The output shows glycemic dysfunction at historical times. Providing an output comprises providing a visualization showing at least one of a behavioral impact of the glycemic dysfunction, historical CGM and insulin data vs. replay simulated CGM with optimal boluses at historical bolus times, or historical CGM and insulin data vs. replay simulated CGM with optimal boluses at estimated meal times. The output comprises a visualization of a compliance of the patient with an ideal pre-meal bolus timing. Meal management information is provided to the subject based on the amount of glycemic dysfunction. Meal management information comprises pre-bolus timing information for the patient. Pre-bolus timing information comprises a recommendation to the patient regarding bolusing before a type of meal in the future.

In an implementation, a system for determining an amount of glycemic dysfunction. The system comprises a data processor that receives continuous glucose monitoring (CGM) and insulin data pertaining to a subject, wherein the CGM and insulin data comprise an insulin bolus amount and a timing for the insulin bolus amount, a replay analyzer that generates a replay analysis using the CGM and insulin data, a quantifier that quantifies an amount of glycemic dysfunction using the replay analysis, and an output device that provides an output representative of the amount of glycemic dysfunction.

Implementations may include some or all of the following features. A first portion of the CGM and insulin data is estimated and a second portion of the CGM and insulin data is reported. The CGM and insulin data comprise at least one of an estimated timing of a meal of the subject or an estimated composition of the meal of the subject. The CGM and insulin data comprise misinformation about at least one of a timing of a meal of the subject or a composition of the meal of the subject. A portion of the CGM and insulin data is received from a computing device of the subject. The CGM and insulin data comprise estimated metabolic states in time series form, a reconciled meal history, and a delivered insulin history. The CGM and insulin data comprise estimated metabolic states, reconciled estimated metabolic inputs, and known metabolic inputs. The CGM and insulin data is discretized in time.

Implementations may also include some or all of the following features. The replay analyzer isolates an impact of timing, carbohydrate counting, and carbohydrate ratio of an estimated bolusing with respect to a meal. The replay analyzer uses replay simulation analysis to assess an impact of numerically optimal boluses at historical bolus times by removing inaccurate carbohydrate counts and inappropriate carbohydrate ratios. The replay analyzer assesses an impact of numerically optimal boluses at estimated historical meal times. The replay analyzer performs replay simulations with at least one of historical CGM and insulin data, numerically optimal boluses at historical bolus times, or numerically optimal boluses at estimated meal times. The replay analyzer is configured to generate a set of candidate boluses, simulate future blood glucose (BG) values associated with each candidate bolus, score a simulated BG trajectory for each candidate bolus using a risk analysis, such as a velocity dependent risk analysis, pick and implement the best bolus based on the score of each candidate bolus, and continue to replay simulate until the time of the next bolus.

Implementations may also include some or all of the following features. The quantifier quantifies the amount of dysfunction of estimated bolusing compared to an optimally timed bolusing. The quantifier quantifies the amount of dysfunction of historical bolusing compared to an optimally timed bolusing. The quantifier quantifies a compliance of the patient with an ideal pre-meal bolus timing.

Implementations may also include some or all of the following features. The output comprises at least one of a plot or a visualization. The output comprises a risk index comprising at least one of high blood glucose risk, low blood glucose risk, or total glycemic risk. The output comprises a number and an extent of excursions into an out-of-range blood glucose level. The output shows glycemic dysfunction at historical times. The output device provides a visualization showing at least one of a behavioral impact of the glycemic dysfunction, historical CGM and insulin data vs. replay simulated CGM with optimal boluses at historical bolus times, or historical CGM and insulin data vs. replay simulated CGM with optimal boluses at estimated meal times. A compliance engine is provided that is configured to provide a visualization of a compliance of the patient with an ideal pre-meal bolus timing. The output device provides meal management information to the subject based on the amount of glycemic dysfunction. Meal management information comprises pre-bolus timing information for the patient. Pre-bolus timing information comprises a recommendation to the patient regarding bolusing before a type of meal in the future.

In an implementation, a method of determining an amount of glycemic dysfunction is provided. The method comprises receiving historical blood glucose (BG) data and historical insulin data at a replay analyzer, performing a plurality of replay analyses for historical boluses and for estimated meals using the historical BG data and the historical insulin data, performing at least one insulin on board (IOB) data analysis using at least one of the plurality of replay analyses, performing at least one BG data analysis using at least one of the plurality of replay analyses, performing at least one discrepancy analysis and at least one comparison using the at least one IOB data analysis and the at least one BG data analysis, and providing an output based on the at least one discrepancy analysis and the at least one comparison.

Implementations may include some or all of the following features. The BG data and insulin data comprise an insulin bolus amount and a timing for the insulin bolus amount. A first portion of the BG data and insulin data is estimated and a second portion of the BG data and insulin data is reported. The BG data and insulin data comprise at least one of an estimated timing of a meal of a subject or an estimated composition of the meal of a subject. The BG data and insulin data comprise misinformation about at least one of a timing of a meal of a subject or a composition of the meal of a subject. A portion of the BG data and insulin data is received from a subject. The BG data and insulin data comprise estimated metabolic states in time series form, a reconciled meal history, and a delivered insulin history. The BG data and insulin data comprise estimated metabolic states, reconciled estimated metabolic inputs, and known metabolic inputs. The BG data and insulin data is discretized in time.

Implementations may also include some or all of the following features. Performing the replay analyses comprises isolating an impact of timing, carbohydrate counting, and carbohydrate ratio of an estimated bolusing with respect to a meal. Performing the replay analyses comprises using replay simulation analysis to assess an impact of numerically optimal boluses at historical bolus times by removing inaccurate carbohydrate counts and inappropriate carbohydrate ratios. Performing the replay analyses comprises assessing an impact of numerically optimal boluses at estimated historical meal times. Performing the replay analyses comprises performing replay simulations at times of historical boluses or at times in advance of estimated meals. Performing the replay analyses comprises performing replay simulations with at least one of the BG data and insulin data, numerically optimal boluses at historical bolus times, or numerically optimal boluses at estimated meal times. Performing the replay analyses comprises: generating a set of candidate boluses; simulating future blood glucose (BG) values associated with each candidate bolus; scoring a simulated BG trajectory for each candidate bolus using a risk analysis; picking and implementing the best bolus based on the score of each candidate bolus; and continuing to replay simulate until the time of the next bolus. The risk analysis is a velocity dependent risk analysis. Performing the at least one discrepancy analysis comprises quantifying an amount of dysfunction of estimated bolusing compared to an optimally timed bolusing. Performing the at least one discrepancy analysis comprises quantifying an amount of dysfunction of historical bolusing compared to an optimally timed bolusing. Performing the at least one discrepancy analysis comprises quantifying a compliance of a patient with an ideal pre-meal bolus timing.

Implementations may also include some or all of the following features. The output comprises at least one of a plot or a visualization. The output comprises a risk index comprising at least one of high blood glucose risk, low blood glucose risk, or total glycemic risk. The output comprises a number and an extent of excursions into an out-of-range blood glucose level. The output shows glycemic dysfunction at historical times. Providing the output comprises providing a visualization showing at least one of a behavioral impact of the glycemic dysfunction, BG data and insulin data vs. replay simulated BG data with optimal boluses at historical bolus times, or BG data and insulin data vs. replay simulated BG data with optimal boluses at estimated meal times. The output comprises a visualization of a compliance of a patient with an ideal pre-meal bolus timing. Providing meal management information to the subject based on an amount of glycemic dysfunction. The meal management information comprises pre-bolus timing information for a patient. The pre-bolus timing information comprises a recommendation to the patient regarding bolusing before a type of meal in the future.

In an implementation, a system for determining an amount of glycemic dysfunction. The system comprises an input device configured to receive blood glucose (BG) data, insulin data, and a plurality of functions, a replay analyzer configured to receive the BG data, the insulin data, and the plurality of functions, and perform a plurality of replay analyses for historical boluses and for estimated meals using the BG data, the insulin data, and the plurality of functions, an insulin on board (IOB) assessor configured to perform a plurality of IOB assessments using at least one of the insulin data or the plurality of replay analyses, a BG risk profiler configured to perform a plurality of BG risk profiles using at least one of the BG data or the plurality of replay analyses, an IOB profiler configured to perform a plurality of IOB profiles using at least one of the plurality of IOB assessments, a BG risk comparator configured to determine at least one of a risk profile plot or a BG risk score using the output of the BG risk profiler, a discrepancy analyzer configured to perform a plurality of discrepancy analyses using the IOB profiles and the IOB assessments to determine at least one of an IOB profile plot, an IOB discrepancy plot, or an IOB trace similarity score, and an output device configured to output at least one of the risk profile plot, the BG risk score, the IOB profile plot, the IOB discrepancy plot, or the IOB trace similarity score.

Implementations may include some or all of the following features. The BG data and insulin data comprise an insulin bolus amount and a timing for the insulin bolus amount. A first portion of the BG data and insulin data is estimated and a second portion of the BG data and insulin data is reported. The BG data and insulin data comprise at least one of an estimated timing of a meal of a subject or an estimated composition of the meal of a subject. The BG data and insulin data comprise misinformation about at least one of a timing of a meal of a subject or a composition of the meal of a subject. A portion of the BG data and insulin data is received from a computing device of a subject. The BG data and insulin data comprise estimated metabolic states in time series form, a reconciled meal history, and a delivered insulin history. The BG data and insulin data comprise estimated metabolic states, reconciled estimated metabolic inputs, and known metabolic inputs. The BG data and insulin data is discretized in time.

Implementations may also include some or all of the following features. The replay analyzer isolates an impact of timing, carbohydrate counting, and carbohydrate ratio of an estimated bolusing with respect to a meal. The replay analyzer uses replay simulation analysis to assess an impact of numerically optimal boluses at historical bolus times by removing inaccurate carbohydrate counts and inappropriate carbohydrate ratios. The replay analyzer assesses an impact of numerically optimal boluses at estimated historical meal times. The replay analyzer performs replay simulations at times of historical boluses or at times in advance of estimated meals. The replay analyzer performs replay simulations with at least one of the BG data and insulin data, numerically optimal boluses at historical bolus times, or numerically optimal boluses at estimated meal times. The replay analyzer is configured to: generate a set of candidate boluses; simulate future blood glucose (BG) values associated with each candidate bolus; score a simulated BG trajectory for each candidate bolus using a risk analysis; pick and implement the best bolus based on the score of each candidate bolus; and continue to replay simulate until the time of the next bolus. The risk analysis is a velocity dependent risk analysis. The discrepancy analyzer quantifies the amount of dysfunction of estimated bolusing compared to an optimally timed bolusing. The discrepancy analyzer quantifies the amount of dysfunction of historical bolusing compared to an optimally timed bolusing. The discrepancy analyzer quantifies a compliance of a patient with an ideal pre-meal bolus timing.

Implementations may also include some or all of the following features. The output comprises at least one of a plot or a visualization. The output comprises a risk index comprising at least one of high blood glucose risk, low blood glucose risk, or total glycemic risk. The output comprises a number and an extent of excursions into an out-of-range blood glucose level. The output shows glycemic dysfunction at historical times. The output device provides a visualization showing at least one of a behavioral impact of the glycemic dysfunction, BG data and insulin data vs. replay simulated BG data with optimal boluses at historical bolus times, or historical BG data and insulin data vs. replay simulated CGM with optimal boluses at estimated meal times. The output device is configured to provide a visualization of a compliance of a patient with an ideal pre-meal bolus timing. The output device provides meal management information to a subject based on the amount of glycemic dysfunction. The meal management information comprises pre-bolus timing information for a patient. The pre-bolus timing information comprises a recommendation to a patient regarding bolusing before a type of meal in the future.

In an implementation, a method of providing a recommendation based on glycemic risk is provided. The method comprises receiving at least one of historical blood glucose (BG) data or historical insulin data for a subject, wherein the BG data and insulin data comprise an insulin bolus amount and a timing for the insulin bolus amount, determining a first risk score for glycemic dysfunction for the subject based on the at least one of the historical BG data or the historical insulin data, receiving at least one of optimal BG data or optimal insulin data for the subject, determining a second risk score for glycemic dysfunction for the subject based on the at least one of the optimal BG data or the optimal insulin data, comparing the first risk score with the second risk score, and outputting a recommendation based on the comparison of the first risk score with the second risk score.

Implementations may include some or all of the following features. A first portion of the BG data and insulin data is estimated and a second portion of the BG data and insulin data is reported. The BG data and insulin data comprise at least one of an estimated timing of a meal of the subject or an estimated composition of the meal of the subject. The BG data and insulin data comprise misinformation about at least one of a timing of a meal of the subject or a composition of the meal of the subject. A portion of the BG data and insulin data is received from the subject. The BG data and insulin data comprise estimated metabolic states in time series form, a reconciled meal history, and a delivered insulin history. The BG data and insulin data comprise estimated metabolic states, reconciled estimated metabolic inputs, and known metabolic inputs. The BG data and insulin data is discretized in time.

Implementations may also include some or all of the following features. Comparing the first risk score with the second risk score comprises quantifying an amount of dysfunction of estimated bolusing compared to an optimally timed bolusing. Comparing the first risk score with the second risk score comprises quantifying an amount of dysfunction of historical bolusing compared to an optimally timed bolusing. Comparing the first risk score with the second risk score comprises quantifying a compliance of a patient with an ideal pre-meal bolus timing.

Implementations may also include some or all of the following features. The recommendation comprises at least one of a plot or a visualization. The recommendation comprises a risk index comprising at least one of high blood glucose risk, low blood glucose risk, or total glycemic risk. The recommendation comprises a number and an extent of excursions into an out-of-range blood glucose level. The recommendation shows glycemic dysfunction at historical times. Outputting the recommendation comprises providing a visualization showing at least one of a behavioral impact of the glycemic dysfunction, BG data and insulin data vs. replay simulated BG data with optimal boluses at historical bolus times, or BG data and insulin data vs. replay simulated BG data with optimal boluses at estimated meal times. The recommendation comprises a visualization of a compliance of a patient with an ideal pre-meal bolus timing.

Implementations may also include some or all of the following features. The method further comprises providing meal management information to the subject based on an amount of glycemic dysfunction. The meal management information comprises pre-bolus timing information for a patient. The pre-bolus timing information comprises a recommendation to the patient regarding bolusing before a type of meal in the future. The method further comprises converting one or more blood glucose values into a relative risk score consistent with the risk of diabetic complications or degree of glycemic control. Each of the first risk score and the second risk score is assigned to a single value or summarized over a time segment such as a daily average risk score. The method further comprises when the first risk score is close to the second risk score, identifying a subject behavior and encouraging the subject behavior because the amount of insulin and timing are close to ideal. When the comparison of the first risk score with the second risk score is at least one of less than a predetermined percentage difference, within a score range or difference, or less than a threshold difference, then further comprising identifying a subject behavior and encouraging the subject behavior because the amount of insulin and timing are close to ideal. The method further comprises when the first risk score is significantly larger than the second risk score, adjusting the amount or timing of the insulin bolus for similar meals in the future. When the comparison of the first risk score with the second risk score is at least one of greater than or equal to a predetermined percentage difference, outside of a score range or difference, equal to or larger than a threshold difference, then further comprising adjusting the amount or timing of the insulin bolus for similar meals in the future.

In an implementation, a method of evaluating glycemic risk is provided. The method comprises determining a historical risk score for glycemic dysfunction based on at least one of historical blood glucose (BG) data or historical insulin data, wherein the historical BG data and historical insulin data comprise an insulin bolus amount and a timing for the insulin bolus amount, determining an optimal risk score for glycemic dysfunction based on at least one of optimal BG data or optimal insulin data, determining a difference between the historical risk score and the optimal risk score, and providing a recommendation based on the difference and based on a threshold.

Implementations may include some or all of the following features. A first portion of the BG data and insulin data is estimated and a second portion of the BG data and insulin data is reported. The BG data and insulin data comprise at least one of an estimated timing of a meal of a subject or an estimated composition of the meal of a subject. The BG data and insulin data comprise misinformation about at least one of a timing of a meal of a subject or a composition of the meal of a subject. A portion of the BG data and insulin data is received from a subject. The BG data and insulin data comprise estimated metabolic states in time series form, a reconciled meal history, and a delivered insulin history. The BG data and insulin data comprise estimated metabolic states, reconciled estimated metabolic inputs, and known metabolic inputs. The BG data and insulin data is discretized in time. Determining a difference between the historical risk score and the optimal risk score comprises quantifying an amount of dysfunction of estimated bolusing compared to an optimally timed bolusing. Determining a difference between the historical risk score and the optimal risk score comprises quantifying an amount of dysfunction of historical bolusing compared to an optimally timed bolusing. Determining a difference between the historical risk score and the optimal risk score comprises quantifying a compliance of a patient with an ideal pre-meal bolus timing.

Implementations may also include some or all of the following features. The recommendation comprises at least one of a plot or a visualization. The recommendation comprises a risk index comprising at least one of high blood glucose risk, low blood glucose risk, or total glycemic risk. The recommendation comprises a number and an extent of excursions into an out-of-range blood glucose level. The recommendation shows glycemic dysfunction at historical times. Providing the recommendation comprises providing a visualization showing at least one of a behavioral impact of the glycemic dysfunction, BG data and insulin data vs. replay simulated BG data with optimal boluses at historical bolus times, or BG data and insulin data vs. replay simulated BG data with optimal boluses at estimated meal times. The recommendation comprises a visualization of a compliance of a patient with an ideal pre-meal bolus timing.

Implementations may also include some or all of the following features. The method further comprises providing meal management information to a subject based on an amount of glycemic dysfunction. The meal management information comprises pre-bolus timing information for a patient. The pre-bolus timing information comprises a recommendation to the patient regarding bolusing before a type of meal in the future. The method further comprises converting one or more blood glucose values into a relative risk score consistent with the risk of diabetic complications or degree of glycemic control. Each of the historical risk score and the optimal risk score is assigned to a single value or summarized over a time segment such as a daily average risk score. The method further comprises when the historical risk score is close to the optimal risk score, identifying a subject behavior and encouraging the subject behavior because the amount of insulin and timing are close to ideal. When the difference between the historical risk score with the optimal risk score is at least one of less than a predetermined percentage difference, within a score range or difference, or less than a threshold difference, then further comprising identifying a subject behavior and encouraging the subject behavior because the amount of insulin and timing are close to ideal. The method further comprises when the historical risk score is significantly larger than the optimal risk score, adjusting the amount or timing of the insulin bolus for similar meals in the future. When the difference between the historical risk score with the optimal risk score is at least one of greater than or equal to a predetermined percentage difference, outside of a score range or difference, equal to or larger than a threshold difference, then further comprising adjusting the amount or timing of the insulin bolus for similar meals in the future.

In an implementation, a method comprises computing a first IOB trace based on a record of actual boluses, computing a second IOB trace of optimal treatments, comparing the first IOB trace with the second IOB trace to determine an IOB similarity score, and using the IOB similarity score to change at least one of smart alert behavior, user recommendations, report features, and visualizations.

Implementations may include some or all of the following features. Comparing the traces comprises determining an inner product between unit magnitude traces to give a value ranging 0 to 1, where 1 indicates actual and optimal dosing is most similar in shape. The method further comprises thresholding or comparing the IOB similarity score to current behavior, and using the thresholding or comparing to change smart alert behavior, user recommendations, report features, and visualizations.

In an implementation, a system comprises a discrepancy analyzer configured to determine an IOB similarity score using a comparison of a first IOB trace based on a record of actual boluses and a second IOB trace of optimal treatments; and an output device configured to output the IOB similarity score.

Implementations may include some or all of the following features. The system further comprises an input device configured to compute the first IOB trace based on a record of actual boluses, and compute the second IOB trace of optimal treatments.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for determining an amount of glycemic dysfunction, the system comprising:
    a replay analyzer configured to (i) receive at least one of historical blood glucose (BG) data obtained from a glucose monitor or historical insulin data obtained from an insulin device for a subject, wherein the BG data and insulin data comprise an insulin bolus amount and a timing for the insulin bolus amount and (ii) determine at least one of optimal BG data or optimal insulin data for the subject;
    a BG risk profiler configured to determine (i) a first risk score for glycemic dysfunction for the subject based on the at least one of the historical BG data or the historical insulin data and (ii) a second risk score for glycemic dysfunction for the subject based on the at least one of the optimal BG data or the optimal insulin data;
    a discrepancy analyzer configured to compare the first risk score with the second risk score; and
    an output device configured to provide a visualization of a recommendation that includes compliance of the subject with an ideal pre-meal bolus timing based on the comparison of the first risk score with the second risk score.

2. The system of claim 1, wherein a first portion of the BG data and insulin data is estimated and a second portion of the BG data and insulin data is reported.

3. The system of claim 1, wherein the BG data and insulin data comprise at least one of an estimated timing of a meal of the subject or an estimated composition of the meal of the subject.

4. The system of claim 1, wherein the BG data and insulin data comprise misinformation about at least one of a timing of a meal of the subject or a composition of the meal of the subject.

5. The system of claim 1, wherein a portion of the BG data and insulin data is received from the subject.

6. The system of claim 1, wherein the BG data and insulin data comprise estimated metabolic states in time series form, a reconciled meal history, and a delivered insulin history.

7. The system of claim 1, wherein the BG data and insulin data comprise estimated metabolic states, reconciled estimated metabolic inputs, and known metabolic inputs.

8. The system of claim 1, wherein the BG data and insulin data is discretized in time.

9. The system of claim 1, wherein the discrepancy analyzer is further configured to quantify an amount of dysfunction of estimated bolusing compared to an optimally timed bolusing.

10. The system of claim 1, wherein the discrepancy analyzer is further configured to quantify an amount of dysfunction of historical bolusing compared to an optimally timed bolusing.

11. The system of claim 1, wherein the discrepancy analyzer is further configured to quantify a compliance of a patient with an ideal pre-meal bolus timing.

12. The system of claim 1, wherein the recommendation comprises at least one of a plot or a visualization.

13. The system of claim 1, wherein the recommendation comprises a risk index comprising at least one of high blood glucose risk, low blood glucose risk, or total glycemic risk.

14. The system of claim 1, wherein the recommendation comprises a number and an extent of excursions into an out-of-range blood glucose level.

15. The system of claim 1, wherein the recommendation shows glycemic dysfunction at historical times.

16. The system of claim 1, wherein the output device is further configured to provide a visualization showing at least one of a behavioral impact of the glycemic dysfunction, BG data and insulin data vs. replay simulated BG data with optimal boluses at historical bolus times, or BG data and insulin data vs. replay simulated BG data with optimal boluses at estimated meal times.

17. The system of claim 1, wherein the output device is further configured to provide meal management information to the subject based on an amount of glycemic dysfunction.

18. The system of claim 17, wherein the meal management information comprises pre-bolus timing information for a patient.

19. The system of claim 18, wherein the pre-bolus timing information comprises a recommendation to the patient regarding bolusing before a type of meal in the future.

20. The system of claim 1, wherein the BG risk profiler is further configured to convert one or more blood glucose values into a relative risk score consistent with the risk of diabetic complications or degree of glycemic control.

21. The system of claim 1, wherein each of the first risk score and the second risk score is assigned to a single value or summarized over a time segment such as a daily average risk score.

22. The system of claim 1, wherein the output device is further configured to encourage subject behavior when the first risk score is close to the second risk score, because the amount of insulin and timing are close to ideal.

23. The system of claim 1, wherein the output device is further configured to encourage subject behavior when the comparison of the first risk score with the second risk score is at least one of less than a predetermined percentage difference, within a score range or difference, or less than a threshold difference, because the amount of insulin and timing are close to ideal.

24. A system for evaluating glycemic risk, the system comprising:

a BG risk profiler configured to (i) determine a historical risk score for glycemic dysfunction based on at least one of historical blood glucose (BG) data obtained from the glucose monitor or historical insulin data obtained from the insulin device for a subject, wherein the historical BG data and historical insulin data comprise an insulin bolus amount and a timing for the insulin bolus amount and (ii) determine an optimal risk score for glycemic dysfunction based on at least one of optimal BG data or optimal insulin data;

a discrepancy analyzer configured to determine a difference between the historical risk score and the optimal risk score; and an output device configured to provide a visualization of a recommendation based on the difference and based on a threshold, wherein the recommendation includes compliance of the subject with an ideal pre-meal bolus timing.

25. The system of claim 24, wherein a first portion of the BG data and insulin data is estimated and a second portion of the BG data and insulin data is reported.

26. The system of claim 24, wherein the BG data and insulin data comprise at least one of an estimated timing of a meal of a subject or an estimated composition of the meal of a subject.

27. The system of claim 24, wherein the BG data and insulin data comprise misinformation about at least one of a timing of a meal of a subject or a composition of the meal of a subject.

28. The system of claim 24, wherein a portion of the BG data and insulin data is received from a subject.

29. The system of claim 24, wherein the BG data and insulin data comprise estimated metabolic states in time series form, a reconciled meal history, and a delivered insulin history.

30. The system of claim 24, wherein the BG data and insulin data comprise estimated metabolic states, reconciled estimated metabolic inputs, and known metabolic inputs.

31. The system of claim 24, wherein the BG data and insulin data is discretized in time.

32. The system of claim 24, wherein the discrepancy analyzer is further configured to quantify an amount of dysfunction of estimated bolusing compared to an optimally timed bolusing.

33. The system of claim 24, wherein the discrepancy analyzer is further configured to quantify an amount of dysfunction of historical bolusing compared to an optimally timed bolusing.

34. The system of claim 24, wherein the discrepancy analyzer is further configured to quantify a compliance of a patient with an ideal pre-meal bolus timing.

35. The system of claim 24, wherein the recommendation comprises at least one of a plot or a visualization.

36. The system of claim 24, wherein the recommendation comprises a risk index comprising at least one of high blood glucose risk, low blood glucose risk, or total glycemic risk.

37. The system of claim 24, wherein the recommendation comprises a number and an extent of excursions into an out-of-range blood glucose level.

38. The system of claim 24, wherein the recommendation shows glycemic dysfunction at historical times.

39. The system of claim 24, wherein the output device is further configured to provide a visualization showing at least one of a behavioral impact of the glycemic dysfunction, BG data and insulin data vs. replay simulated BG data with optimal boluses at historical bolus times, or BG data and insulin data vs. replay simulated BG data with optimal boluses at estimated meal times.

40. The system of claim 24, wherein the recommendation comprises a visualization of a compliance of a patient with an ideal pre-meal bolus timing.

41. The system of claim 24, wherein the output device is further configured to provide meal management information to a subject based on an amount of glycemic dysfunction.

42. The system of claim 41, wherein the meal management information comprises pre-bolus timing information for a patient.

43. The system of claim 42, wherein the pre-bolus timing information comprises a recommendation to the patient regarding bolusing before a type of meal in the future.

44. The system of claim 24, wherein the BG risk profiler is further configured to convert one or more blood glucose values into a relative risk score consistent with the risk of diabetic complications or degree of glycemic control.

45. The system of claim 24, wherein each of the historical risk score and the optimal risk score is assigned to a single value or summarized over a time segment such as a daily average risk score.

46. The system of claim 24, wherein the output device is further configured to encourage subject behavior when the historical risk score is close to the optimal risk score because the amount of insulin and timing are close to ideal.

47. The system of claim 24, wherein the output device is further configured to encourage subject behavior when the difference between the historical risk score with the optimal risk score is at least one of less than a predetermined percentage difference, within a score range or difference, or less than a threshold difference, because an amount of insulin and timing are close to ideal.

48. The system of claim 24, wherein, when the difference between the historical risk score with the optimal risk score is at least one of greater than or equal to a predetermined percentage difference, outside of a score range or difference, equal to or larger than a threshold difference, the output device is further configured to cause adjustment of an amount or timing of the insulin bolus for similar meals in the future.

* * * * *